United States Patent [19]

Chatterjee et al.

[11] Patent Number: 4,855,320

[45] Date of Patent: Aug. 8, 1989

[54] 5-ARYLALKYL-4-ALKOXY-2(5H)-FURANONES, INTERMEDIATES AND PROCESSES FOR THE PREPARATION THEREOF AND MEDICAMENTS CONTAINING THEM

[75] Inventors: Shyam S. Chatterjee, Karlsruhe; Klaus Klessing, Ettlingen, both of Fed. Rep. of Germany

[73] Assignee: Dr. Willmar Schwabe GmbH & Company, Karlsruhe, Fed. Rep. of Germany

[21] Appl. No.: 46,586

[22] Filed: May 4, 1987

[30] Foreign Application Priority Data

May 5, 1986 [DE] Fed. Rep. of Germany ....... 3615157

[51] Int. Cl.$^4$ ..................... A61K 31/34; C07D 307/32
[52] U.S. Cl. ................................... 514/473; 549/313; 560/104; 562/470
[58] Field of Search ................. 549/313, 323; 514/473

[56] References Cited

U.S. PATENT DOCUMENTS 4,585,789  4/1986  Okamoto et al. .................. 549/313
4,613,613  9/1986  Oguri et al. ......................... 549/323

FOREIGN PATENT DOCUMENTS 1920176  10/1970  Fed. Rep. of Germany ...... 549/313

OTHER PUBLICATIONS

Hansel, R. et al., "Behavior of 5-Hydroxykawain Derivatives under Mild Alkaline Conditions", Z. Naturforsch, 33b, pp. 1020–1025 (1978).
Pelter et al, "The Synthesis of Piperolide and Related Compds," Tetrahedron Letters, No. 18, pp. 1627–1630, 1979.

*Primary Examiner*—Glennon H. Hollrah
*Attorney, Agent, or Firm*—Frost & Jacobs

[57] ABSTRACT

The present invention provides 5-arylalkyl-4-alkoxy-2(5H)-furanones of the formula:

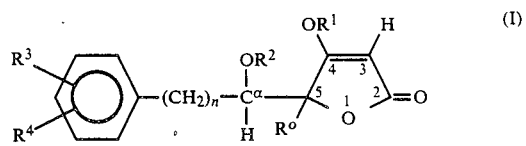

wherein the oxygen atoms on C-5 and C-α, relative to one another, are in the threo-position, with the exclusion of those compounds of the formula (I) wherein $R^2$ is H or $CH_3$ when n=0 or 2, $R^o$=H, $R^1$=$CH_3$, $R^3$=H and $R^4$=H.

The present invention also provides processes for their preparation, as well as new 3-alkoxy-5-(subst.)-phenyl-2(E), 4(E)-pentadienoates as reactive intermediates for the preparation of the new furanone derivatives.

The new furanone derivatives of the threo series are active as anticonvulsives/anti-epileptics. Therefore, the present invention also provides medicaments which contain these new furanone derivatives, as well as known furanones, the anticonvulsive/anti-epileptic effectiveness of which has been found for the first time.

17 Claims, No Drawings

5-ARYLALKYL-4-ALKOXY-2(5H)-FURANONES, INTERMEDIATES AND PROCESSES FOR THE PREPARATION THEREOF AND MEDICAMENTS CONTAINING THEM

BACKGROUND OF THE INVENTION

The present invention is concerned with new 5-arylalkyl-4-alkoxy-2(5H)-furanones, processes and intermediates for the preparation thereof and pharmaceutical compositions containing them.

The new 5-arylalkyl-4-alkoxy-2(5H)-furanones according to the present invention are compounds of the formula:

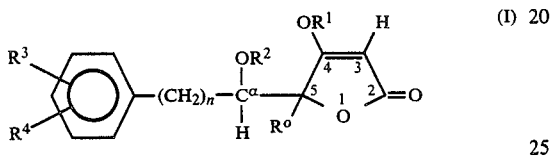

wherein the oxygen atoms on C-5 and C-α, relative to one another, are in the threo-position and wherein n is 0, 1 or 2, $R^o$ is a hydrogen atom or an alkyl radical containing up to 3 carbon atoms, $R^1$ a straight-chained or branched alkyl radical containing up to 5 carbon atoms, $R^2$ is a hydrogen atom, an alkyl radical containing up to 3 carbon atoms or the radical

wherein $R^5$ is an alkyl radical containing up to 5 carbon atoms or an ethoxyethyl or methoxyethyl radical and $R^6$ is a hydrogen atom, an alkyl radical containing up to 5 carbon atoms or a methoxymethyl radical, $R^3$ and $R^4$, independently of one another, are hydrogen, fluorine, chlorine or bromine atoms, alkyl radicals containing up to 3 carbon atoms, perfluoroalkyl radicals containing up to 3 carbon atoms, a difluoromethoxy radical or a nitro group, with the exclusion of those compounds of formula (I), wherein $R^2$ is H or $CH_3$ when n=0 or 2, $R^o$=H, $R^1$=$CH_3$, $R^3$=H and $R^4$=H.

Furthermore, the present invention provides intermediates and processes for the preparation of the above-mentioned compounds, as well as the use of these compounds as therapeutic active materials and also medicaments which contain the mentioned compounds and the compounds excluded from the scope of protection by the disclaimer.

Since the compounds of formula (I) with the asymmetric carbon atoms C-5 and C-α contain two chirality centres in their molecule, there are two diastereomeric pairs, namely, the two threo enantiomers:

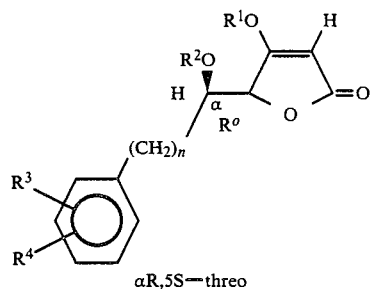

αR,5S—threo

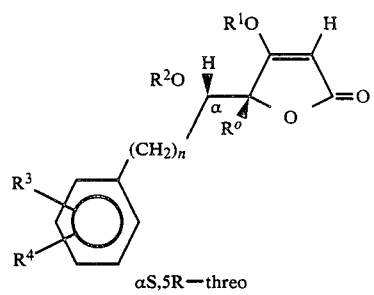

αS,5R—threo and the two erythro enantiomers:

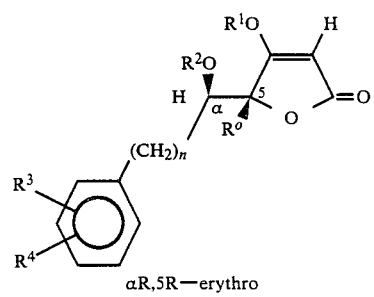

αR,5R—erythro

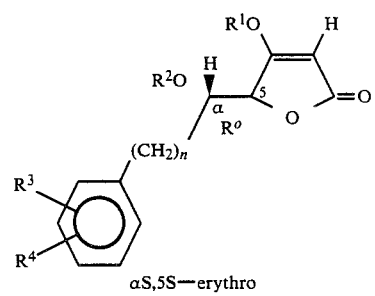

αS,5S—erythro

The present invention is concerned exclusively with the two threo-enantiomers which can be present in the form of their racemate or of their two laevo or dextrorotatory optical antipodes, as well as with processes which lead stereoselectively to the threo-enantiomers.

The compounds excluded by disclaimer from the product protection are known:
4-methoxy-5-phenylhydroxymethyl-2(5H)-furanone was described by A. Pelter et al., Tetrahedron Lett., 1979, p. 1627–1630;
4-methoxy-5-[methoxy-(phenyl)-methyl]-2(5H)-furanone by A. Pelter et al., Tetrahedron Lett., 1982, p. 5229–5232;
4-methoxy-5-(α-hydroxy-γ-phenylpropyl)-2(5H)-furanone and 4-methoxy-5-(α-methoxy-γ-phenylpropyl)-2(5H)-furanone were described by R. Hansel et al., Z. Naturforsch., 33b, p. 1020–1025 (1978).

However, the authors did not report anything about a pharmacological effectiveness or even of a therapeutic utility of the known compounds.

For the preparation of the known compounds, R. Hänsel et al. loc. cit. suggest the isolation of 5,6-Z-piperolide from the species *Piper sanctum* indigenous to Mexico which can be converted by photon irradiation into the stereoisomeric 5,6-E-piperolide. By catalytic hydrogenation, 5,6-E-piperolide can be reacted to give 5,6-threo-tetrahydropiperolide (4-methoxy-5-(α-methoxy-γ-phenylpropyl)-2(5H)-furanone). However, obtaining the starting material, i.e. the natural product 5,6-Z-piperolide, and its conversion into 5,6-E-piperolide is very expensive and, therefore, unsuitable for a commercial use.

Another known process for the preparation of the known compounds (cf. A. Pelter et al., Tetrahedron Lett., 1979, p. 1627–1630) starts from methyl tetronate, the preparation of which is known from European patent specification No. 10,288. Methyl tetronate is hereby mixed with lithium diisopropylamide with the formation of a carbanion and then reacted at −78° C. with benzaldehyde or dihydrocinnamic aldehyde. Quite apart from the fact that the reaction conditions (−78° C.!) are unsuitable for an economic preparation on a large scale, in the case of this process there always result mixtures of the threo and erythro diastereomers so that, for the separation of the threo compounds in pure form, laborious purification operations are necessary, insofar as the separation succeeds at all. Furthermore, the lithium organic compound employed is self-inflammatory and the hexamethylphosphoric acid triamide (HMPA) added as solubiliser is carcinogenic.

A series of variants of the process described by A. Pelter et al. are also known which, however, all possess the same principal disadvantages since they lead non-stereoselectively to one of the two diastereomeric pairs and, because of the necessary low temperatures, are very energy expensive.

Finally, a large series of compounds of the most differing chemical constitution with anticonvulsive and anti-epileptic effectiveness are also ready known (cf., for example, Ehrhart/Ruschig, Arzneimittel, Vol. 1, p. 177 et seq., pub. Verlag Chemie, Weinheim, 1972) to which belong, in particular, the active materials carbamazepine, diazepam, diphenylhydantoin, ethosuximide, phenobarbital and valproic acid. All these known anticonvulsives/anti-epileptics display chronic-toxic side effects to varying degrees, including exanthema, depressive states, paranoia, megaloblastic anaemia, damage of the blood-forming bone marrow, liver damage and others.

Therefore, there is a need for new pharmaceutical agents with anticonvulsive and anti-epileptic effectiveness because only thus is the physician able to select from a larger source of medicaments those agents the activity and side-effect spectra of which best satisfy the physical and psychic needs of the patients.

SUMMARY OF THE INVENTION

It is an object of the present invention to satisfy this need by making available new compounds with anticonvulsive/anti-epileptic effectiveness. Furthermore, the present invention provides processes for the preparation of such compounds with anticonvulsive/anti-epileptic effectiveness with which it is possible to synthesise stereoselectively the threo enantiomers either in the form of their racemates or in the form of their individual optical antipodes.

The solution of these objects consists in the provision and making available of the compounds according to the present invention with anticonvulsive/anti-epileptic effectiveness, as well as medicaments containing these compounds and in the provision of the processes according to the present invention for the preparation of these materials.

The subject of the present invention are thus, first, the initially mentioned 5-arylalkyl-4-alkoxy-2(5H)-furanones of formula (I) as defined in claim 1, namely, not only in the form of their DL-racemates but also in the form of the two optical anti-podes (D- and L-form) which can be prepared from the racemates according to conventional methods for the resolution of racemates into optically pure forms.

The compounds of the threo series according to the present invention display a surprisingly good anticonvulsive/anti-epileptic effectiveness, whereas the corresponding compounds of the erythro series are inactive in comparable dosage. The compounds according to the present invention can be used for the treatment of epilepsy in humans.

BRIEF DESCRIPTION OF THE DRAWING

The drawing is a flow chart of reactions embodying the method of the invention.

DETAILED DESCRIPTION OF THE INVENTION

Preferred compounds according to the present invention include:

4-methoxy-5-(phenylhydroxymethyl)-2(5H)-furanones of the formula II

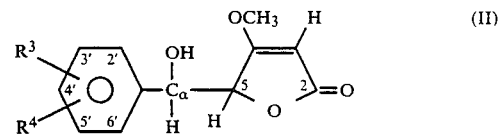

wherein the oxygen atoms on C-5 and C-α, relatively to one another, are in the threo-position and wherein one of the two symbols $R^3$ and $R^4$ represents a hydrogen atom and the other a fluorine, chlorine or bromine atom in the 2'-position or a methyl, trifluoromethyl or nitro group in the 2'-position;

4-methoxy-5-(phenylhydroxymethyl)-2(5H)-furanones of formula (II), wherein the oxygen atoms on C-5 and C-α, relatively to one another, are in the threo-position and wherein one of the two symbols $R^3$ and $R^4$ is a fluorine, chlorine or bromine atom or a trifluoromethyl radical, each in the 2'-position, and the other is a chlorine or bromine atom or a trifluoromethyl radical, in each case in the 4'-, 5'- or 6'-position;

4-methoxy-5-[methoxy-(phenyl)-methyl]-2(5H)-furanones of the formula III

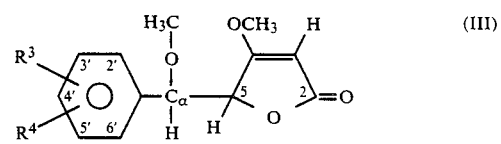

wherein the oxygen atoms on C-5 and C-α, relatively to one another, are in the threo-position and wherein $R^3$ and R⁴ have the above-given meanings but with the exclusion of those compounds of formula (III) wherein both symbols R³ and R⁴ represent hydrogen atoms;

4-methoxy-5-(phenylmethyl)-2(5H)-furanones of the formula IV

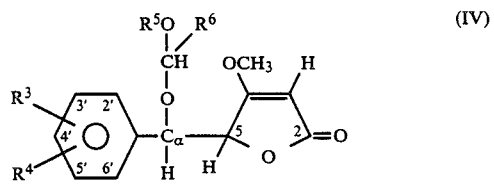

wherein the oxygen atom on C-5 and C-α, relatively to one another, are in the threo-position and wherein $R^5$ is a methyl or methoxyethyl radical and $R^3$, $R^4$ and $R^6$ have the meanings as given in claim 1.

Because of their good anticonvulsive/anti-epileptic effectiveness, the following compounds according to the present invention are especially preferred:

threo-5-(2'-chlorophenylhydroxymethyl)-4-methoxy-2(5H)-furanone;
threo-5-(2'-bromophenylhydroxymethyl)-4-methoxy-2(5H)-furanone;
threo-5-(2'-fluorophenylhydroxymethyl)-4-methoxy-2(5H)-furanone;
threo-5-(2'-trifluoromethylphenylhydroxymethyl9-4-methoxy-2(5H)-furanone
threo-5-(2',5'-dichlorophenyl)hydroxymethyl-4-methoxy-2(5H)-furanone;
threo-5-(2',4'-dichlorophenyl)hydroxymethyl-4-methoxy-2(5H)-furanone;
threo-4-methoxy-5-[methoxymethoxy-(2'-chlorophenyl)methyl]-2(5H)-furanone;
threo-4-methoxy-5-[methoxymethoxy-(2'-bromophenyl)methyl]-2(5H)-furanone;
threo-4-methoxy-5-[methoxymethoxy-(2'-fluorophenyl)methyl]-2(5H)-furanone;
threo-4-methoxy-5-[methoxymethoxy-(2'-trifluoromethylphenyl)-methyl]-2(5H)-furanone;
threo-4-methoxy-5-[methoxy-(2'-chlorophenyl)-methyl]-2(5H)-furanone.

The present invention also provides 3-alkoxy-5-(subst.)-phenyl-2(E),4(E)-pentadienoates of the formula IX

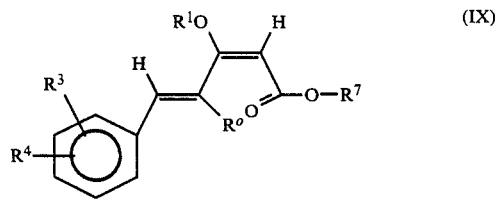

wherein $R^o$, $R^1$, $R^3$ and $R^4$ have the meanings as given in claim 1 and $R^7$ is a hydrogen atom, a straight-chained or branched alkyl radical containing up to 10 carbon atoms or an aralkyl radical containing 7 to 10 carbon atoms.

These new compounds of formula (IX) are reactive intermediates which can be used for the preparation of the compounds of formula (I) according to the present invention.

In the case of a preferred group of the abovementioned reactive intermediates of formula (IX), $R^7$ is a hydrogen atom, a straight-chained or branched alkyl radical containing up to 4 carbon atoms or a benzyl radical.

Finally, the present invention provides a process for the preparation of those compounds of the formula (I), wherein n is 0, which is characterised by the combination of the following process steps:

(A) A benzaldehyde of the formula VI:

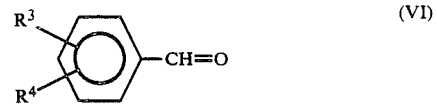

wherein R³ and R⁴ have the meanings as given above when explaining the formula I, is condensed with a 3-alkoxy-2(E)-alkenoic acid lower alkyl ester of the formula VII:

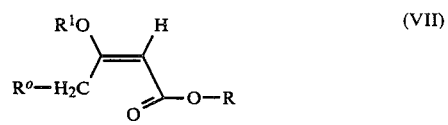

wherein $R^o$ and $R^1$ have the meanings as given above when explaining the formula I and R is an alkyl radical containing up to 4 carbon atoms, with hydrolytic splitting off of the residue R, stereo-selectively to give the correspondingly substituted 2(E),4(E)-pentadienoic acid of the formula VIII:

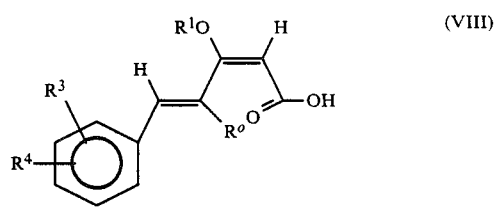

wherein $R^o$, $R^1$, $R^3$ and $R^4$ have the above-given meanings;

(B) the so obtained pentadienoic acid is converted into an ester of the formula IX:

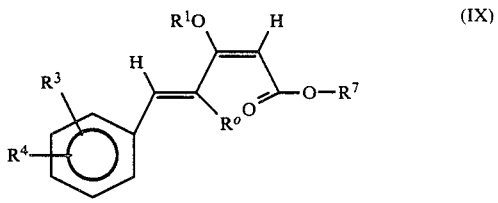

wherein $R^7$ is a straight-chained or branched alkyl radical containing up to 10 carbon atoms or an aralkyl radical containing 7 to 10 carbon atoms;

(C) the ester of formula (IX) is reacted by cis-dihydroxylation by means of catalytic amounts of osmium tetroxide and of an oxidation agent to give the corresponding 3-alkoxy-4,5(threo)-dihydroxy-5-(R³,R⁴-subst.)-phenyl-2(E)-pentenoic acid ester of the formula XI:

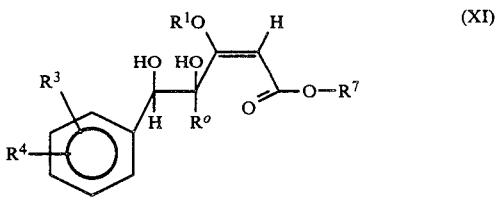

(D) from which, with 1,4-elimination of the alcohol $R^7OH$, there is formed the corresponding threo-4-alkoxy-5-[($R^3$,$R^4$-subst.)-phenylhydroxymethyl]-2(5H)-furanone of formula (I) with $R^2$=H;

(E) which is subsequently optionally reacted with a reactive compound of the general formula $R^2$—X, wherein $R^2$ has the meaning as given above when explaining the formula I, with the exception of hydrogen, and X is a reactive group, for example a halogen atom or an alkoxy radical, with the splitting off of X-H to give the corresponding compound of formula (I) with $R^2 \neq H$.

Advantageous embodiments of the process according to the present invention consist in that the condensation in the step (A) is carried out in a dipolar aprotic solvent and in a basic medium;

the condensation is carried out in dimethyl sulphoxide/water, with the addition of an alkali metal hydroxide, a quaternary ammonium base or a mixture thereof;

the condensation is carried out under an inert gas atmosphere at a temperature of from about 70° to 140° C.;

in step (C) there are used alkyl hydroperoxides, tertiary amine-N-oxides or chlorates as oxidation agents;

the dihydroxylation is carried out in step (C) in the presence of a quaternary ammonium base or of a quaternary ammonium salt.

In a further embodiment of the process according to the present invention, the pentadienoic acid of the formula (VIII) formed in step (A) is subjected to the cis-dihydroxylation according to step (C) with the formation of the corresponding substituted pentenoic acid of the formula (XI), with $R^7$=H, whereafter the pentenoic acid is reacted according to step (D) with 1,5-elimination of water to give the corresponding furanone of the formula (I), with $R^2$=H, which is subsequently optionally reacted according to step (E) to give a compound of the formula (I) with $R^2 \neq H$.

The process according to the present invention for the preparation of those compounds of the formula (I) wherein n is 0 is explained in the following with reference to the accompanying drawing (formula scheme):

PROCESS STEP A

For the synthesis of the 3-alkoxy-5-($R^3$,$R^4$-subst.)-phenyl-2(E),4(E)-pentadienoic acids of the formula (VIII), the benzaldehydes of the formula (VI) are condensed with the 3-alkoxy-2(E)-alkenoic acid lower alkyl esters of the formula (VII), preferably in a dipolar aprotic solvent and especially in dimethyl sulphoxide, at an elevated temperature and with the addition of an alkali metal hydroxide and of a quaternary ammonium base or aqueous solutions thereof and, after completion of the condensation and cooling the reaction mixture, the 3-alkoxy-5-($R^3$,$R^4$-subst.)-phenyl-2(E),4(E)-pentadienoic acids formed are precipitated out by dilution with water and acidification.

Especially good yields are achieved when the following reaction conditions are maintained: To 1 mole of aldehyde of the formula (VI) are added 100 to 500 ml. dimethyl sulphoxide and 0.5 to 2 mole 3-alkoxy-2(E)-alkenoic acid lower alkyl ester of the formula (VII), as well as 0.01 to 1 mole of a quaternary ammonium base or of a quaternary ammonium salt, optionally in the form of an aqueous solution.

Under an inert gas atmosphere, for example under nitrogen or argon, the reaction mixture is heated to a temperature of from about 70° to 140° C., and preferably of from about 90° to 110° C., and an amount of alkali metal hydroxide is added thereto which is at least equimolar to the amount of ester of the formula (VII) used, optionally in the form of a concentrated aqueous solution, and the mixture is stirred preferably for about 2 to 12 hours at the said temperature.

After cooling to ambient temperature, the pentadienoic acids of the formula (VIII) are precipitated out by dilution with water and acidification to a pH of about 1 to 4, filtered off, washed with water and subsequently with a lower alcohol and optionally dried.

As benzaldehydes of the formula (VI), wherein $R^3$ and $R^4$, independently of one another, are hydrogen, fluorine, chlorine or bromine atoms, $C_1$- to $C_3$-alkyl radicals, $C_1$- to $C_3$-perfluoroalkyl radicals, difluoromethoxy radicals or nitro groups, there can, for example, be used the following compounds: benzaldehyde, benzaldehydes substituted in the 2-, 3- or 4-position by fluorine, chlorine, bromine, methyl, trifluoromethyl, difluoromethoxy or nitro, 2,4-, 2,5-, 2,6-, 3,4- or 3,5-dichlorobenzaldehyde, 2,4- or 2,5-dibromobenzaldehyde, 2,4-, 2,5- or 3,5-bis-(trifluoromethyl)benzaldehyde, 2-chloro-4-bromobenzaldehyde, 2-chloro-5-bromobenzaldehyde, 2-chloro-4-trifluoromethylbenzaldehyde, 2-chloro-5-trifluoromethylbenzaldehyde, 2-bromo-5-trifluoromethylbenzaldehyde, 2-trifluoromethyl-4-chlorobenzaldehyde, 2-trifluoromethyl-5-chlorobenzaldehyde, 2-fluoro-4-chlorobenzaldehyde, 2-fluoro-5-trifluoromethylbenzaldehyde or the like.

Preferably, there are used benzaldehyde and those monosubstituted benzaldehydes which carry one of the substituents $R^3$ or $R^4$ in the 2-position. Furthermore, there are preferably used those disubstituted benzaldehydes which, in the 2-position, carry a fluorine, chlorine or bromine atom or a perfluoroalkyl radical and in the 4- or 5-position a chlorine or bromine atom or a trifluoromethyl radical.

The benzaldehydes of the formula (VI) are known or can be prepared according to known methods (cf. Methodicum chimicum, Vol. 5, pp. 203–336, pub. Georg Thieme Verlag, Stuttgart, 1975).

The 3-alkoxy-2(E)-alkenoic acid lower alkyl esters of the formula (VII), wherein "lower alkyl" is an alkyl radical containing up to 5 carbon atoms and $R^1$ is a straight-chained or branched alkyl radical containing up to 5 carbon atoms, are also known or can be prepared according to known methods. Preferred esters of the formula (VII) are those methyl or ethyl esters in which $R^1$ is an alkyl radical containing up to 3 carbon atoms, for example 3-methoxy-2(E)-butenoic acid methyl or ethyl ester, 3-ethoxy-2(E)-butenoic acid methyl or ethyl ester, 3-propoxy-2(E)-butenoic acid methyl or ethyl ester, 3-isopropoxy-2(E)-butenoic acid methyl or ethyl ester, as well as the homologous 3-alkoxy-2(E)-pentenoic, hexenoic or heptenoic acid esters. Especially preferred are 3-methoxy-2(E)-butenoic acid ethyl ester and 3-ethoxy-2(E)-butenoic acid ethyl ester.

For the achievement of high yields, in the case of the condensation in step A of the process according to the present invention, there are added quaternary ammonium bases, optionally in the form of aqueous solutions, as catalysts. For this purpose, there are especially preferred the quaternary tetraalkyl or trialkylphenyl or trialkylbenzyl-ammonium hydroxides, which are known as phase transfer catalysts, for example tetraethyl or tetrabutyl-ammonium hydroxide, benzyltriethyl or -trimethyl-ammonium hydroxide, or dodecyltrimethyl-ammonium hydroxide. Instead of the quaternary ammonium bases, there can also be used the salts thereof with mineral acids, for example the chlorides, sulphates, hydrogen sulphates or bromides thereof, with the addition of an equivalent amount of concentrated aqueous potassium or sodium hydroxide solution.

The condensation in step A of the process according to the present invention always leads, with simultaneous ester hydrolysis, to the 4,5-trans-configurational pentadienoic acid derivatives of the formula (VIII), which could be demonstrated with the use of conventional physical methods. When $R^o$ is a hydrogen atom, the coupling constants of the H-4 and H-5 protons in the $^1$H-NMR spectrum are, for example, about 15 to 17 Hz.

PROCESS STEP B

The pentadienoic acid derivatives of the formula (VIII) are converted in known manner into the esters of the formula (IX), wherein $R^7$ is a $C_1$- to $C_{10}$-alkyl radical or a $C_7$- to $C_{10}$-arylalkyl radical (cf., for example, Methodicum chimicum, loc. cit., Vol. 5, p. 637–677 (1975)).

PROCESS STEP C-1

For the selective cis-dihydroxylation of the C-4/C-5 double bond, the pentadienoic acid esters of the formula (IX) are reacted in the presence of catalytic amounts of osmium tetroxide in an appropriate inert solvent with an oxidation agent. A survey of such per se known oxidation processes is to be found in M. Schröder, Chem. Rev., 80, pp. 187–213 (1980).

As oxidation agent, there is preferably used an alkyl hydroperoxide or an aliphatic, cycloaliphatic or heterocycloaliphatic amine-N-oxide, for example N-methylmorpholine-N-oxide, preferably in the form of a concentrated aqueous solution. As inert solvents for the oxidation reaction, there can be used tertiary alkanols, lower alkanones, lower alkyl alkanoates or lower chlorinated hydrocarbons.

PROCESS STEP D-1

From the compounds of the formula (XI) obtained in step C-1, by intramolecular γ-lactone formation with the splitting off of the alcohols $R^7OH$, wherein $R^7$ has the above-given meanings, there can be produced the threo-4-alkoxy-5-(phenylhydroxymethyl)-2(5H)-furanones of the formula (XII), wherein $R^o$, $R^1$, $R^3$ and $R^4$ have the above-given meanings. Depending upon the reaction conditions and the nature of the residue $R^7$, the lactone formation can take place wholly or partly already during the reaction in step C-1 or during the working up of the reaction mixture of step C-1. In weakly acidic medium, the lactone ring closes especially easily with elimination of the alcohol $R^7OH$.

PROCESS STEP C-2

Instead of the esters of the formula (IX), the acids of general formula (VIII) can also be directly subjected to the cis-dihydroxylation catalysed by osmium tetroxide. The reaction then leads directly to the 4,5-(threo)-dihydroxy-2(E)-pentenoic acid derivatives of the formula (X), wherein $R^o$, $R^1$, $R^3$ and $R^4$ have the above-given meanings. As oxidation agents, there can be used the compounds described in step C-1.

In this case, too, the oxidation reaction is preferably carried out with an alkyl hydroperoxide in the presence of quaternary ammonium bases, e.g. in the presence of tetraethyl- or tetrabutyl-ammonium hydroxide; the quaternary ammonium bases quaternary ammonium bases increase the solubility of the sparingly soluble pentadienoic acids of the formula (VIII) in aqueous media and improve the catalytic action of the osmium tetroxide.

In the same way as in step C-1, also in step C-2 the 4,5(threo)-dihydroxy compounds are always obtained stereoselectively.

PROCESS STEP D-2

Analogously to the γ-lactone formation in step D-1, the intramolecular ring closure of the 4,5(threo)-dihydroxy acids of the formula (X) obtained in step C-2 takes place, with the splitting off of water, to give the corresponding 2(5H)-furanone derivatives of the formula (XII) at least partly already during the course of the oxidation reaction in step C-2 but especially when the working up of the reaction mixture of step C-2 takes place in a neutral or acidic medium.

PROCESS STEP E

For the preparation of those compounds of the formula (I) according to the present invention, wherein n=0 and $R^2 \neq H$, the threo-4-alkoxy-5-phenylhydroxymethyl-2(5H)-furanones of the formula (XII), wherein $R^o$, $R^1$, $R^3$ and $R^4$ have the above-given meanings, obtained in step D-1 or D-2 are reacted in known manner to give the correspondingly substituted $R^2$ derivatives of the formula (XIII), which are ethers or acetals.

(a) Ether derivatives of the formula (XIII)

For the preparation of the ethers, in which $R^2$ is an alkyl radical containing up to 3 carbon atoms, the compounds of the formula (XII) are reacted in a lower alkanone, preferably in acetone or butanone, at a temperature of from about 50° to 100° C. or under reflux with a $C_1$- to $C_3$-alkyl iodide, preferably with methyl iodide, in the presence of at least an equimolar amount of silver(I) oxide.

(b) Acetal derivatives of the formula (XIII)

For the preparation of the acetals, in which $R^2$ is the radical

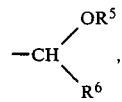

wherein $R^5$ is an alkyl radical containing up to 5 C-atoms or an ethoxyethyl or methoxyethyl radical and $R^6$ is a hydrogen atom, an alkyl radical containing up to 5 carbon atoms or a methoxymethyl radical, the compounds of the formula (XII) are reacted with a compound of the formula XIV:

(XIV)

wherein $R^5$ and $R^6$ have the above-given meanings and X is a methoxy or ethoxy radical, in the presence of a catalytic amount of p-toluenesulphonic acid and in the presence of 0.1 to 1 equivalent, referred to the amount of (XII), of lithium bromide. This method is, in principle, described by J.-L. Gras et al., Synthesis, 1985, p. 74.

Preferred acetal derivatives of the formula (XIII) are those in which $R^2$ is a methoxymethyl, ethoxymethyl, methoxyethoxymethyl, α-ethoxypropyl or α,β-dimethoxyethyl radical.

The processes described for the preparation of ethers and acetals in step E only represent exemplary methods; for this purpose, there can, of course, also be employed other known methods of etherification or acetalisation.

For the preparation of those compounds of the formula (I) according to the present invention, wherein n is 0, 1 or 2, there is used analogously the process described by A. Pelter et al. in Tetrahedron Lett. 1979, pp. 1627–1630. For this purpose, the 4-alkoxy-5(2H)-furanones which, being derived from tetronic acid, can also be called alkyl tetronates, and of the formula (XVII), wherein $R^o$ and $R^1$ have the above-given meanings, are converted by means of appropriate organo-lithium compounds into the lithium derivatives of the formula (XVIII):

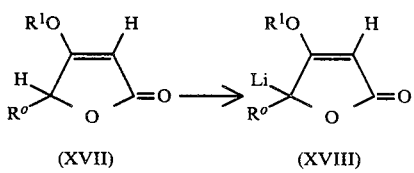

(XVII)       (XVIII)

which are reacted with the aldehydes of the formula (XIX):

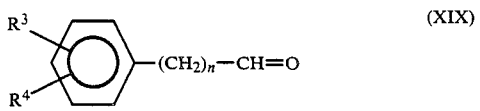
(XIX)

wherein $R^3$ and $R^4$ have the above-given meanings and n is 0, 1 or 2, to give compounds of the formula (I), wherein n, $R^o$, $R^1$, $R^3$ and $R^4$ have the above-given meanings and $R^2$ is a hydrogen atom.

In the case of this analogous process, there always result mixtures of the threo- and erythro-diastereomers, for which reason the threo compounds must subsequently be isolated in known and laborious manner, for example by fractional crystallisation or by chromatographic processes. There are then obtained the threo compounds of the formula (I), wherein $R^2$ is a hydrogen atom, which can possibly be subsequently subjected according to step E to an etherification or acetalisation.

The alkyl tetronates of the formula (XVII) are either known from the literature or can be prepared according to known processes (cf. e.g. EP-PS 10 288; J. Org. Chem., 49, 927–928/1984; Tetrahedron, 35, 2181–2185/1979; Tetrahedron, 34, 1453–1455/1978; Synth. Commun., 10, 805–811/1980; Angew. Chem., 94, 651–652/1982).

As further method for the preparation of the alkyl tetronates of the formula (XVII) employed as starting material in the case of this process, there was found the base-catalysed transalkoxylation of 4-methoxy-2(5H)-furanones. For this purpose, the methoxyfuranones of the formula (XVII), wherein $R^1$ is a methyl radical, are reacted with an excess of an alkanol $R^1OH$, wherein $R^1$ is a $C_2$- to $C_5$-alkyl radical, with the addition of a catalytic amount of the corresponding alkali metal alcoholate $R^1ONa$ or $R^1OK$, whereby, with the splitting off of methanol, there results the desired 4-alkoxy-2(5H)-furanones of the formula (XVII), in which $R^1$ is an alkyl radical containing 2 to 5 carbon atoms.

The present invention also provides medicaments which, optionally together with a pharmaceutically inert excipient, contain at least one of the compounds of the formula (I), including those wherein $R^2$=H or $CH_3$ when n=0 or 2, $R^o$=H, $R^1$=$CH_3$, $R^3$=H and $R^4$=H.

These medicaments and pharmaceutical compositions can be used as anticonvulsives in human and veterinary medicine and as anti-epileptics in human medicine. The effective dose in which the compounds can be administered is, not only in human medicine but also in veterinary medicine, from about 0.05 to 3 mg./kg. 5–200 mg. of the active substance can be administered orally one or more times daily.

As pharmacologically inert, conventional carrier or additive materials, there can be used, for example, water, vegetable oils, polyethylene glycols, glycerol esters, gelatine, carbohydrates, such as lactose or starch, magnesium stearate, talc, petroleum jelly, preserving agents, stabilisers, lubricants, wetting agents, emulsifiers, physiologically acceptable salts, buffer substances, colouring materials, flavouring materials and aroma materials. The selection of the pharmacologically inert excipient depends upon whether the active materials are to be administered enterally, parenterally or topically. The new and known compounds of the formula (I) can also be administered in admixtue with other active materials, for example vitamins or other known anticonvulsives or antiepileptics.

Each of the compounds according to the present invention and the intermediates mentioned in the following Examples are agents especially appropriate for the preparation of pharmaceutical compositions.

In the following Examples, the following abbreviations are used:

m.p.=melting point (uncorrected)
b.p.=boiling point (uncorrected)
(d)=decomposition Temperatures are given in °C. and pressures are given in bar (mbar), whereby 1 bar (mbar)≙$10^5$ ($10^2$) Pa.

The 300 MHz-$^1$H- and 75.46 MHz-$^{13}$C-nuclear resonance spectra were recorded on an NMR spectrometer WH 300 of the firm Bruker. As solvent herefor, DMSO-$D_6$ was used, insofar as nothing otherwise is stated. The chemical displacements δ are given in ppm relative to the tetramethylsilane signal (internal standard).

EXAMPLE 1

Ethyl 3-methoxy-2(E)-butenoate

A mixture of 520 g. (4 mole) ethyl acetoacetate, 400 ml. methanol and 2 ml. 36% hydrochloric acid (or 1 ml. concentrated sulphuric acid) is warmed to 50° C. With stirring, there is added dropwise thereto 425 g. (4 mole) trimethyl orthoformate in such a manner that the mixture is kept at about 50° C. Subsequently, the methyl formate formed and excess methanol are distilled off and the residue is fractionated over a Vigreux column. Between 184° and 186° C. there distil over 548 g. (3.8 mole) pure ethyl 3-methoxy-2(E)-butenoate. Yield: 95%.

EXAMPLE 2

Ethyl 3-ethoxy-2(E)-butenoate

Preparation analogous to Example 1 by reacting ethyl acetoacetate with triethyl orthoformate in ethanol with hydrochloric acid as catalyst. Yield: 84.5%. B.p. 191°–195° C. M.p.=31°–33° C.

EXAMPLE 3

Methyl 3-methoxy-2(E)-pentenoate

Preparation analogous to Example 1 by reacting methyl 3-oxopentenoate with trimethyl orthoformate in methanol and sulphuric acid as catalyst. Yield: 87.7%. B.p.=76°–78° C. (20 mbar).

EXAMPLE 4

Ethyl 3-methoxy-2(E)-hexenoate

Preparation analogous to Example 1 by reacting ethyl 3-oxohexanoate with trimethyl orthoformate in methanol with sulphuric acid as catalyst. Yield: 95.8%. B.p.=87°–89° C. (20 mbar).

EXAMPLE 5

Ethyl 3-methoxy-5-methyl-2(E)-hexenoate

Preparation analogous to Example 1 by reacting ethyl 5-methyl-3-oxohexanoate with trimethyl orthoformate in methanol with sulphuric acid as catalyst. Yield: about 50%. B.p.=91°–97° C. (16–19 mbar).

EXAMPLE 6

3-Methoxy-5-phenyl-2(E),4(E)-pentadienoic acid

Method a 11.6 g. (0.05 mole) benzyltriethylammonium chloride are added, with stirring and under a nitrogen atmosphere, to a mixture of 53 g. (0.5 mole) benzaldehyde, 100 ml. dimethyl sulphoxide and 72 g. (0.5 mole) ethyl 3-methoxy-2(E)-butenoate and thereafter a solution of 33.6 g. (0.6 mole) potassium hydroxide in 35 ml. water is added dropwise thereto. The reaction mixture is heated for about 16 hours to 110° C., the solution is evaporated, the residue is dissolved in 400 ml. water and starting materials and by-products are extracted with 100 ml. dichloromethane. From the aqueous phase, after acidification with 70 ml. 10M hydrochloric acid, the crude product precipitates out which, after filtering off with suction, washing acid-free with water, recrystallisation from ethanol and drying at 100° C. in a vacuum, gives 34.9 g. (0.171 mole) of pure product; m.p. 154°–155° C. Yield: 34.2%. Literature m.p.=157.7°–158° C. (E. E. Smissman and A. N. Voldeng, J. Org. Chem., 29, 3161/1964).

Analysis: $C_{12}H_{12}O_3$ (204.23) calc.: C (70.57), H (5.92) found: C (70.49), H (6.16)

Method b

With stirring and under a nitrogen atmosphere, to a solution of 3785 g. (26.25 mole) ethyl 3-methoxy-2(E)-butenoate in 6 liters dimethyl sulphoxide are successively added dropwise 2653 g. (25 mole) benzaldehyde and 926 ml. (2.5 mole) 40% aqueous tetraethylammonium hydroxide. After heating to 100° C., there is added dropwise thereto a solution of 1470 g. (26.25 mole) potassium hydroxide in 1500 ml. water, followed by stirring for 4 hours at 100° C. After cooling to about 20° C., the mixture is poured in 50 liters of water and impurities are extracted with 10 liters dichloromethane. The aqueous phase is acidified, with vigorous stirring, with about 3 liters 33% hydrochloric acid to pH 2 and the precipitated crude product is filtered off over a pressure filter, washed chloride-free with water and blow dried with nitrogen. The filter cake is suspended in 6 liters ethanol, again filtered and, after blow drying, dried in a vacuum up to the end temperature of 85° C. to give 3071 g. (15.04 mole) of pure product; m.p. 159°–160° C. Yield: 60.1%.

EXAMPLE 7

5-(2-Chlorophenyl)-3-methoxy-2(E),4(E)-pentadienoic acid 3785 g. (26.25 mole) ethyl 3-methoxy-2(E)-butenoate are reacted analogously to Example 6b in 6 liters dimethyl sulphoxide with 3515 g. (25 mole) 2-chlorobenzaldehyde, 926 ml. (2.5 mole) 40% tetraethylammonium hydroxide and 2940 g. (26.25 mole) 50% aqueous potassium hydroxide solution and then stirred for 4 hours at 100° C. After cooling, the reaction mixture is diluted with 10 liters of water and by-products are extracted with 10 liters dichloromethane. The aqueous phase is stirred into a mixture of 3 liters 33% hydrochloric acid and 50 liters water, whereafter the pH value is 3.5 to 4. The precipitated crude product is, after filtering, washing with water until free of chloride and blow drying, again suspended in 20 liters ethanol, filtered off with suction, blow dried and dried up to the end temperature of 85° C. at 20 mbar to give 5045 g. (21.14 mole) of pure product; m.p. 202° C. Yield: 84.55%

Analysis: $C_{12}H_{11}ClO_3$ (238.67) calc.: C (60.39), H (4.65), Cl (14.85) found: C (60.33), H (4.85), Cl (14.72)

300 MHz-$^1$H-NMR: 11.8–12.2 (1H, br.m., COOH), 8.08 (1H, d, $J_{5/4}$=16 Hz, H-5), 7.54 (1H, d, $J_{4/5}$=16 Hz, H-4), 5.29 (1H, s, H-2), 3.785 (3H, s, OCH$_3$), 7.35–7.75 (4H, m, aromat. protons).

Analogously to the synthesis methods used in Examples 6a, b and 7, by condensation of benzaldehyde or substituted benzaldehydes with the 3-alkoxy-2(E)-alkenoates described in Examples 1 to 5, there are prepared the 3-alkoxy-5-(subst.)-phenyl-2(E),4(E)-pentadienoic acids set out in Table 1. Tables 2 and 3 give the analytical and $^1$H-NMR spectroscopic data.

TABLE 1

| | 3-Alkoxy-5-phenylpentadienoic acids | | |
|---|---|---|---|
| Example No. | designation | yield [%] + | m.p. [°C.] (recrystallised from) |
| 8 | 5-(2-chlorophenyl)-3-ethoxy-2(E),4(E)-pentadienoic acid | 41 | 179–181 (ethanol) |
| 9 | 5-(2-chlorophenyl)-3-methoxy-4-methyl-2(E),4(E)-pentadienoic acid | 24 | 126–128 (methanol) |
| 10 | 5-(2-chlorophenyl)-4-ethyl-3-methoxy-2(E),4(E)-pentadienoic acid | 8.3 | 131–132 (ethanol) |
| 11 | 5-(2-chlorophenyl)-4-isopropyl-3-methoxy-2(E),4(E)-pentadienoic acid | | |
| 12 | 5-(4-chlorophenyl)-3- | 36 | 200 |

TABLE 1-continued

3-Alkoxy-5-phenylpentadienoic acids

| Example No. | designation | yield [%] + | m.p. [°C.] (recrystallised from) |
|---|---|---|---|
| | methoxy-2(E),4(E)-pentadienoic acid | | (ethanol) |
| 13 | 5-(2-bromophenyl)-3-methoxy-2(E),4(E)-pentadienoic acid | 71 | 206–207 (ethanol) |
| 14 | 5-(3-bromophenyl)-3-methoxy-2(E),4(E)-pentadienoic acid | 14 | 161–163 (ethanol) |
| 15 | 5-(2-fluorophenyl)-3-methoxy-2(E),4(E)-pentadienoic acid | 66 | 188–190 (ethanol) |
| 16 | 5-(2-trifluoromethylphenyl)-3-methoxy-2(E),4(E)-pentadienoic acid | 15 | 173–174 (ether) |
| 17 | 5-(3-trifluoromethylphenyl)-3-methoxy-2(E),4(E)-pentadienoic acid | 41 | 152–153 (ethanol) |
| 18 | 5-(4-trifluoromethylphenyl)-3-methoxy-2(E),4(E)-pentadienoic acid | 32 | 171–183 (methanol) |
| 19 | 3-methoxy-5-(2-nitrophenyl)-2(E),4(E)-pentadienoic acid | | 209–211 (ethanol) |
| 20 | 3-methoxy-5-(3-nitrophenyl)-2(E),4(E)-pentadienoic acid | 9 | 198–199 |
| 21 | 3-methoxy-5-(2,5-dimethylphenyl)-2(E),4(E)-pentadienoic acid | 49 | 161–162 (ether) |
| 22 | 5-(2-chloro-5-methylphenyl)-3-methoxy-2(E),4(E)-pentadienoic acid | 48 | 179–181 (methanol) |
| 23 | 5-(2,3-dichlorophenyl)-3-methoxy-2(E),4(E)-pentadienoic acid | 10 | 215–216 (ethanol) |
| 24 | 5-(2,4-dichlorophenyl)-3-methoxy-2(E),4(E)-pentadienoic acid | 73 | 196–197 (ethanol) |
| 25 | 5-(2,4-dichlorophenyl)-3-ethoxy-2(E),4(E)-pentadienoic acid | 50 | 198–200 (ethanol) |
| 26 | 5-(2,5-dichlorophenyl)-3-methoxy-2(E),4(E)-pentadienoic acid | 55 | 198–199 (ethanol) |
| 27 | 5-(2,5-dichlorophenyl)-3-ethoxy-2(E),4(E)-pentadienoic acid | 49 | 213–215 (ethanol) |
| 28 | 5-(3,4-dichlorophenyl)-3-methoxy-2(E),4(E)-pentadienoic acid | 46 | 188–190 (ethanol) |
| 29 | 5-(3,5-dichlorophenyl)-3-methoxy-2(E),4(E)-pentadienoic acid | 38 | 211–213 (2-propanol) |
| 30 | 5-[3,5-bis-(trifluoromethyl)-phenyl]-3-methoxy-2(E),4(E)-pentadienoic acid | 6 | 217–219 (chloroform) |
| 31 | 5-(2-chloro-5-trifluoromethylphenyl)-3-methoxy-2(E),4(E)-pentadienoic acid | 40 | 188–192 (ethanol) |
| 32 | 5-(4-chloro-2-trifluoromethylphenyl)-3-methoxy-2(E),4(E)-pentadienoic acid | 22 | 190–193 (ethanol) |
| 33 | 5-(4-bromo-2-chlorophenyl)-3-methoxy-2(E),4(E)-pentadienoic acid | 66 | 192–194 (acetone) |

+ In the case of yields below 50% reaction, working up and recrystallisation conditions not yet optimised.

TABLE 2

| Example No. | sum formula molecular weight | % calc. C % found C | H H | other |
|---|---|---|---|---|
| 8 | $C_{13}H_{13}ClO_3$ 252.69 | 61.79 61.91 | 5.18 5.31 | Cl (14.03) 14.3 |
| 9 | $C_{13}H_{13}ClO_3$ 252.69 | 61.79 61.46 | 5.18 5.15 | Cl (14.03) 13.7 |
| 10 | $C_{14}H_{15}ClO_3$ 266.73 | 63.05 63.16 | 5.67 6.00 | Cl (13.29) 13.5 |
| 12 | $C_{12}H_{11}ClO_3$ 238.67 | 60.39 59.80 | 4.65 4.42 | Cl (14.85) 15.5 |
| 13 | $C_{12}H_{11}BrO_3$ 283.13 | 50.91 51.01 | 3.92 3.38 | Br (28.22) 28.0 |
| 14 | $C_{12}H_{11}BrO_3$ 283.13 | 50.91 50.06 | 3.92 3.90 | Br (28.22) 30.5 |
| 15 | $C_{12}H_{11}FO_3$ 222.22 | 64.86 64.56 | 4.99 4.88 | F (8.55) 7.9 |
| 16 | $C_{13}H_{11}F_3O_3$ 272.23 | 57.36 57.40 | 4.07 4.13 | F (20.94) 20.6 |
| 17 | $C_{13}H_{11}F_3O_3$ 272.23 | 57.36 56.99 | 4.07 3.90 | F (20.94) |
| 18 | $C_{13}H_{11}F_3O_3$ 272.23 | 57.36 57.15 | 4.07 3.91 | F (20.94) |
| 19 | $C_{12}H_{11}NO_5$ 249.23 | 57.83 57.97 | 4.45 4.33 | N (5.62) 5.35 |
| 20 | $C_{12}H_{11}NO_5$ 249.23 | 57.83 58.15 | 4.45 4.66 | N (5.62) 5.73 |
| 21 | $C_{14}H_{16}O_3$ 232.29 | 72.39 72.27 | 6.94 7.32 | |
| 22 | $C_{13}H_{13}ClO_3$ 252.69 | 61.79 62.11 | 5.18 5.15 | Cl (14.03) 14.5 |
| 23 | $C_{12}H_{10}Cl_2O_3$ 273.12 | 52.77 52.78 | 3.69 3.65 | Cl (25.96) 25.7 |
| 24 | $C_{12}H_{10}Cl_2O_3$ 273.12 | 52.77 52.81 | 3.69 3.76 | Cl (25.96) 26.2 |
| 25 | $C_{13}H_{12}Cl_2O_3$ 287.15 | 54.38 54.40 | 4.21 4.19 | Cl (24.69) 24.9 |
| 26 | $C_{12}H_{10}Cl_2O_3$ 273.12 | 52.77 52.90 | 3.69 3.75 | Cl (25.96) 26.2 |
| 27 | $C_{13}H_{12}Cl_2O_3$ 287.15 | 54.38 53.98 | 4.21 3.98 | Cl (24.69) 24.9 |
| 28 | $C_{12}H_{10}Cl_2O_3$ 273.12 | 52.77 52.95 | 3.69 3.84 | Cl (25.96) 26.2 |
| 29 | $C_{12}H_{10}Cl_2O_3$ 273.12 | 52.77 52.64 | 3.69 3.87 | Cl (25.96) 26.2 |
| 30 | $C_{14}H_{10}F_6O_3$ 340.23 | 49.43 48.90 | 2.96 2.88 | F (33.50) |
| 31 | $C_{13}H_{10}ClF_3O_3$ 306.67 | 50.91 49.96 | 3.29 3.11 | Cl (11.56) 11.2 |
| 32 | $C_{13}H_{10}ClF_3O_3$ 306.67 | 50.91 50.74 | 3.29 2.99 | Cl (11.56) 11.5 |
| 33 | $C_{12}H_{10}BrClO_3$ 317.57 | 45.39 45.35 | 3.17 3.00 | Cl (11.16) 10.8 |

TABLE 3

300 MHz - $^1$H - NMR spectroscopy

δ-values [ppm] for

| Example No. | (wide) —COOH | H-2(s) | 3-OCH$_3$(s) | H-4(d) | H-5(d) | $J_{H-4/H-5}$ [Hz] |
|---|---|---|---|---|---|---|
| | | | (3-OCH$_2$—) | | | |
| 8 | 11.96 | 5.25 | 3.99(q) | 7.55 | 8.08 | 16.2 |
| | | | (—CH$_2$—) | | | |
| 10 | 11.46 | 5.17 | 3.7 | 2.34(q) | 6.44 | — |
| 12 | 11.7 | 5.22 | 3.73 | 7.20 | 8.01 | 16.1 |

TABLE 3-continued

| | 300 MHz - $^1$H - NMR spectroscopy | | | | | |
|---|---|---|---|---|---|---|
| | δ-values [ppm] for | | | | | |
| Example No. | (wide) —COOH | H-2(s) | 3-OCH$_3$(s) | H-4(d) | H-5(d) | $J_{H-4/H-5}$ [Hz] |
| 14 | 11.95 | 5.23 | 3.75 | 8.03 | 7.23 | 16.4 |
| 15 | 11.75 | 5.24 | 3.74 | 7.30 | 8.11 | 16.6 |
| 16 | 11.8 | 5.29 | 3.76 | 7.5 | 8.05 | 16.1 |
| 17 | 11.78 | 5.25 | 3.75 | 7.30 | 8.09 | 16.6 |
| 18 | 11.8 | 5.26 | 3.75 | 7.28 | 8.12 | 16.6 |
| 19 | 11.99 | 5.3 | 3.77 | 7.51 | 8.02 | 16.2 |
| 20 | 12.02 | 5.29 | 3.77 | 7.39 | 8.16 | 16.4 |
| 21 | 11.65 | 5.21 | 3.74 | 7.42 | 7.90 | 16.1 |
| 22 | 11.5 | 5.26 | 3.77 | 7.49 | 8.01 | 16.4 |
| 23 | 12 | 5.31 | 3.78 | 7.52 | 8.06 | 16.4 |
| 24 | 12.0 | 5.29 | 3.77 | 7.46 | 8.07 | 15.8 |
| 25 | 12 | 5.26 | (3-OCH$_2$—) 3.99(q) | 7.47 | 8.06 | 16.4 |
| 26 | 12.04 | 5.31 | 3.78 | 7.43 | 8.05 | 16.2 |
| 27 | | 5.27 | (3-OCH$_2$—) 3.99(q) | 7.44 | 8.04 | 15.8 |
| 28 | 12 | 5.25 | 3.75 | 7.22 | 8.03 | 16.4 |
| 29 | 11.8 | 5.27 | 3.74 | 7.19 | 8.11 | 16.1 |
| 31 | 12 | 5.32 | 3.78 | 7.50 | 8.11 | 16.4 |
| 32 | 11.9 | 5.31 | 3.77 | 7.42 | 8.06 | 16.4 |
| 33 | 11.9 | 5.29 | 3.78 | 7.44 | 8.06 | 16.4 |

EXAMPLE 34

Benzyl 5-(2-chlorophenyl)-3-methoxy-2(E),4(E)-pentadienoate

To a mixture of 48 g. (0.2 mole) 5-(2-chlorophenyl)-3-methoxy-2(E),4(E)-pentadienoic acid, 600 ml. acetone and 60 g. (0.43 mole) potassium carbonate are added dropwise, with stirring, 34.2 g. (0.2 mole) benzyl bromide and heated under reflux for 16 hours. After filtering off inorganic residues, evaporation of the filtrate and recrystallisation from tert.-butyl methyl ether, there are obtained 56.1 g. (0.17 mole) of pure benzyl ester; m.p. 83°-86° C. Yield: 85%.

Analysis: $C_{19}H_{17}ClO_3$ (328.80)
calc.: C (69.41), H (5.21), Cl (10.78)
found: C (69.42), H (5.08), Cl (10.9).

EXAMPLE 35

Ethyl 5-(2-chlorophenyl)-3-methoxy-2(E),4(E)-pentadienoate (a) A mixture of 31 g. (0.13 mole) 5-(2-chlorophenyl)-3-methoxy-2(E),4(E)-pentadienoic acid, 400 ml. acetone, 36 g. (0.26 mole) potassium carbonate and 20.8 g. (0.13 mole) ethyl iodide is heated to the boil under reflux for 18 hours. After cooling, filtering and evaporating the filtrate, the oily crude product is taken up in 100 ml. n-pentane, insoluble potassium iodide is filtered off and the filtrate is evaporated and then dried at 45° C. and 20 mbar to give 33.3 g. (0.125 mole) of pure ethyl ester; m.p. 49°-51° C. Yield: 96%.

Analysis: $C_{14}H_{15}ClO_3$ (266.73) calc.: C (63.05), H (5.67), Cl (13.29) found: C (63.37), H (5.69), Cl (13.3)

(b) With stirring, into a mixture of 35 liters butanone, 2386 g. (10 mole) 5-(2-chlorophenyl)-3-methoxy-2(E),4(E)-pentadienoic acid, 2073 g. (15 mole) potassium carbonate and 16.6 g. (0.1 mole) potassium iodide is added dropwise at 56° C. 1635 g. (15 mole) ethyl bromide and then stirred for 24 hours at 56° C. After cooling and filtering off inorganic components, the filtrate is washed twice with 10 liters of water and the butanone phase is evaporated to give 2348 g. (8.80 mole) of ethyl ester, which crystallises upon cooling. Thin layer chromatography and infra-red spectrum show the identity with the product described in Example 35a; m.p. 45° C. Yield: 88%.

EXAMPLE 36

Methyl 5-(2-chlorophenyl)-3-methoxy-2(E),4(E)-pentadienoate

A mixture of 23.9 g. (0.1 mole) 5-(2-chlorophenyl)-3-methoxy-2(E),4(E)-pentadienoic acid, 500 ml. acetone and 30.4 g. (0.22 mole) potassium carbonate is mixed, while stirring, with 9.5 ml. (0.1 mole) dimethyl sulphate and heated under reflux for 4 hours. After cooling and filtering, the filtrate is evaporated, the crude product is dissolved in 100 ml. chloroform, washed twice with 30 ml. water, the chloroform phase is evaporated and the residue recrystallised from isopropanol/water. After drying at 50° C./20 mbar, there are obtained 22.18 g. (87.7 mmole) of pure methyl ester; m.p. 50°-52° C. Yield: 87.8%.

Analysis: $C_{13}H_{13}ClO_3$ (252.69) calc.: C (61.79), H (5.18), Cl (14.03) found: C (61.30), H (5.07), Cl (13.7)

Analogously to the methods described in Examples 34 to 36, there were prepared the 3-alkoxy-5-phenyl-2(E),4(E)-pentadienoic acid esters set out in the following Table 4. Results of the elementary analyses are summarised in Table 5.

TABLE 4

| 3-Alkoxy-5-phenylpentadienoates | | | |
|---|---|---|---|
| Example No. | designation | Yield [%] | m.p. [°C.] (recrystallised from) |
| 37 | isopropyl 5-(2-chlorophenyl)-3-methoxy-2(E),4(E)-pentadienoate | 95 | 55–58 (pentane) |
| 38 | sec.-butyl 5-(2-chlorophenyl)-3-methoxy-2(E),4(E)-pentadienoate | 85 | 41–42 (isopropanol/water) |
| 39 | tert.-butyl 5-(2-chlorophenyl)-3-methoxy-2(E),4(E)-pentadienoate | 30 | oil (evaporated) |
| 40 | ethyl 3-methoxy-5-phenyl-2(E),4(E)-pentadienoate | 96 | 34 (evaporated) |
| 41 | ethyl 5-(2-chlorophenyl)-3-ethoxy-2(E),4(E)-pentadienoate | 85 | 79–81 (methanol) |
| 42 | ethyl 5-(4-chlorophenyl)-3-methoxy-2(E),4(E)-pentadien- | 94 | 52–53 (isopropanol/ |

TABLE 4-continued

3-Alkoxy-5-phenylpentadienoates

| Example No. | designation | Yield [%] | m.p. [°C.] (recrystallised from) |
|---|---|---|---|
| 43 | ethyl 5-(2-bromophenyl)-3-methoxy-2(E),4(E)-pentadienoate | 98 | 45–46 (pentane) |
| 44 | ethyl 5-(2-fluorophenyl)-3-methoxy-2(E),4(E)-pentadienoate | 99 | 46–48 (isopropanol) |
| 45 | ethyl 5-(2-trifluoromethylphenyl)-3-methoxy-2(E),4(E)-pentadienoate | 99 | 75 (ethanol) |
| 46 | ethyl 5-(3-trifluoromethylphenyl)-3-methoxy-2(E),4(E)-pentadienoate | 92 | 46–47 (ethanol) |
| 47 | ethyl 5-(4-trifluoromethylphenyl)-3-methoxy-2(E),4(E)-pentadienoate | 52 | 42–44 (ethanol) |
| 48 | ethyl 3-methoxy-5-(2,5-dimethylphenyl)-2(E),4(E)-pentadienoate | 94 | 53–54 (ethanol) |
| 49 | ethyl 5-(2-chloro-5-methylphenyl)-3-methoxy-2(E),4(E)-pentadienoate | 95 | 76–78 (ethanol) |
| 50 | ethyl 5-(2,3-dichlorophenyl)-3-methoxy-2(E),4(E)-pentadienoate | 78 | 110–111 (ethanol) |
| 51 | ethyl 5-(2,4-dichlorophenyl)-3-methoxy-2(E),4(E)-pentadienoate | 92 | 81–83 (isopropanol) |
| 52 | ethyl 5-(2,4-dichlorophenyl)-3-ethoxy-2(E),4(E)-pentadienoate | 92 | 64–67 (isopropanol) |
| 53 | ethyl 5-(2,5-dichlorophenyl)-3-methoxy-2(E),4(E)-pentadienoate | 92 | 97–98 (ethanol) |
| 54 | ethyl 5-(2,5-dichlorophenyl)-3-ethoxy-2(E),4(E)-pentadienoate | 64 | 87–90 (isopropanol) |
| 55 | ethyl 5-(3,4-dichlorophenyl)-3-methoxy-2(E),4(E)-pentadienoate | 89 | 76–78 (ethanol) |
| 56 | ethyl 5-(3,5-dichlorophenyl)-3-methoxy-2(E),4(E)-pentadienoate | 93 | 89–91 (ethanol) |
| 57 | ethyl 5-[3,5-bis-(trifluoromethyl)-phenyl]-3-methoxy-2(E),4(E)-pentadienoate | 88 | 86–88 (evaporated) |
| 58 | ethyl 5-(2-chloro-5-trifluoromethylphenyl)-3-methoxy-2(E),4(E)-pentadienoate | 76 | 47–50 (ethanol) |
| 59 | ethyl 5-(4-chloro-2-trifluoromethylphenyl)-3-methoxy-2(E),4(E)-pentadienoate | 92 | 79–80 (ethanol/water) |
| 60 | ethyl 5-(4-bromo-2-chlorophenyl)-3-methoxy-2(E),4(E)-pentadienoate | 91 | 91–93 (ethanol) |
| 61 | ethyl 5-(2-chlorophenyl)-3-methoxy-4-methyl-2(E),4(E)-pentadienoate | 98 | oil (evaporated) |
| 62 | ethyl 5-(2-chlorophenyl)-4-ethyl-3-methoxy-2(E),4(E)-pentadienoate | 92 | 49 (ethanol) |
| 63 | ethyl 5-(2-chlorophenyl)-4-isopropyl-3-methoxy-2(E),4(E)-pentadienoate | | |

TABLE 5

Elementary analyses

| Example No. | sum formula molecular weight | % cal. C % found C | H H | other |
|---|---|---|---|---|
| 37 | $C_{15}H_{17}ClO_3$ 280.76 | 64.17 64.38 | 6.10 6.13 | Cl (12.63) 12.3 |
| 38 | $C_{16}H_{19}ClO_3$ 294.78 | 65.19 64.88 | 6.50 6.68 | Cl (12.03) 11.7 |
| 40 | $C_{14}H_{16}O_3$ 232.29 | 72.39 72.85 | 6.94 6.78 | |
| 41 | $C_{15}H_{17}ClO_3$ 280.76 | 64.17 64.12 | 6.10 6.38 | Cl (12.63) 13.0 |
| 42 | $C_{14}H_{15}ClO_3$ 266.73 | 63.05 62.99 | 5.67 5.98 | Cl (13.29) 13.5 |
| 43 | $C_{14}H_{15}BrO_3$ 311.19 | 54.04 53.70 | 4.86 4.83 | Br (25.86) 25.0 |
| 44 | $C_{14}H_{15}FO_3$ 250.28 | 67.19 66.78 | 6.04 5.61 | F (7.59) 7.3 |
| 45 | $C_{15}H_{15}F_3O_3$ 300.29 | 60.00 60.35 | 5.04 5.32 | F (18.98) 17.9 |
| 46 | $C_{15}H_{15}F_3O_3$ 300.29 | 60.00 60.19 | 5.04 5.35 | F (18.98) 18.3 |
| 47 | $C_{15}H_{15}F_3O_3$ 300.29 | 60.00 60.11 | 5.04 5.28 | F (18.98) 17.6 |
| 48 | $C_{16}H_{20}O_3$ 260.34 | 73.82 74.45 | 7.74 7.81 | |
| 49 | $C_{15}H_{17}ClO_3$ 280.76 | 64.17 63.90 | 6.10 6.03 | Cl (12.63) 13.0 |
| 50 | $C_{14}H_{14}Cl_2O_3$ 301.18 | 55.83 56.06 | 4.68 4.57 | Cl (23.54) 23.2 |
| 51 | $C_{14}H_{14}Cl_2O_3$ 301.18 | 55.83 55.80 | 4.68 4.81 | Cl (23.54) 23.8 |
| 52 | $C_{15}H_{16}Cl_2O_3$ 315.21 | 57.16 56.85 | 5.12 5.08 | Cl (22.50) 22.7 |
| 53 | $C_{14}H_{14}Cl_2O_3$ 301.18 | 55.83 55.49 | 4.68 4.73 | Cl (23.54) 23.7 |
| 54 | $C_{15}H_{16}Cl_2O_3$ 315.21 | 57.16 56.73 | 5.12 5.21 | Cl (22.50) 21.5 |
| 55 | $C_{14}H_{14}Cl_2O_3$ 301.18 | 55.83 55.52 | 4.68 4.57 | Cl (23.54) 23.7 |
| 56 | $C_{14}H_{14}Cl_2O_3$ 301.18 | 55.83 55.48 | 4.68 4.85 | Cl (23.54) 23.7 |
| 58 | $C_{15}H_{14}ClF_3O_3$ 334.73 | 53.83 53.43 | 4.22 4.14 | Cl (10.59) 11.7 |
| 60 | $C_{14}H_{14}BrClO_3$ 345.63 | 48.65 48.72 | 4.08 3.95 | Cl (10.26) 10.5 |
| 62 | $C_{16}H_{19}ClO_3$ 294.78 | 65.19 66.29 | 6.50 6.83 | Cl (12.03) 12.2 |

EXAMPLE 64 threo-5-(2-Chlorophenylhydroxylmethyl)-4-methoxy-2(5H)-furanone

On the basis of the synthesis of this compound, there are illustrated the various embodimental forms of the oxidation of the 3-alkoxy-5-phenyl-2(E),4(E)-pentadienoic acid derivatives catalysed by osmium tetroxide to give threo-4-alkoxy-5-phenylhydroxymethyl-2(5H)-furanones (see Scheme 1, steps C-1, C-2, D-1 and D-2).

Process variant a

To a mixture of 48.0 g. (201 mmole) 5-(2-chlorophenyl)-3-methoxy-2(E),4(E)-pentadienoic acid, 400 ml. water and 400 ml. (566 mmole) 20% aqueous tetraethylammonium hydroxide is added, with stirring and cooling to 0° C., 50 ml. of a 0.02M solution of osmium tetroxide in acetone or tert.-butanol and 56 ml. (403 mmole) 70% aqueous tert.-butyl hydroperoxide. After stirring for 6 hours at 0° C., the reaction mixture is left to stand for 8 days at 0°–5° C. and thereafter excess hydroperoxide is reduced by stirring with 10% aqueous sodium sulphite solution. By the addition of 1M sulphuric acid, the pH is adjusted to 2, unreacted starting product thereby crystallising out. This is filtered off with suction (10.1 g.≙42.3 mmole). The filtrate is extracted three times with 100 ml. chloroform and the extract is washed free of quaternary ammonium salts with 50 ml. 1M hydrochloric acid. The extract contains a mixture of threo-5-(2-chlorophenyl)-4,5-dihydroxy-3-methoxy-2(E)-pentenoic acid and threo-5-(2-chlorophenylhydroxymethyl)-4-mehoxy-2(5H)-furanone. By evaporation, the ring closure is completed to give, after recrystallisation from ethyl acetate, 18.12 g. (71.2 mmole) of pure threo-5-(2-chlorophenylhydroxymethyl)-4-methoxy-2(5H)-furanone; m.p. 149°–151° C. Yield referred to reacted starting material: 45.1%.

Analysis: $C_{12}H_{11}ClO_4$ (254.67) calc.: C (56.59), H (4.35), Cl (13.92) found: C (56.27), H (4.35), Cl (14.0)

300 MHz-$^1$-NMR: 7.3–7.7 (4H, m, aromatic protons), 5.96 (1H, d, $J_{OH/Ha}$=5.5 Hz, α-OH), 5.440 (1H, d, $J_{H-3/H-5}$=1.3 Hz, H-3), 5.225 (1H, dd, $J_{Ha/H-5}$=2 Hz, Hα), 5.008 (1H, s, H-5), 3.923 (3H, s, OCH$_3$).

75.46 MHz-$^{13}$C-NMR (broad band decoupled); C-2 (172.530), C-3 (90.268), C-4 (180.229), C-5 (79.872), C-α (66.721), $C_{Ar}$-1' (138.409), $C_{Ar}$-2' to 6' (130.650, 129.571, 129.421, 129.032 and 127.265), OCH$_3$ (60.071).

The assignment of the $^{13}$C-signals was verified by off-resonance and gated spectrum, as well as by SFORD experiments.

Process variant b

To a solution of 26.7 g. (100 mmole) ethyl 5-(2-chlorophenyl)-3-methoxy-2(E),4(E)-pentadienoate in 450 ml. acetone are added 6.5 g. (25 mmole) tetraethylammonium acetate tetrahydrate and successively there is added dropwise thereto, with stirring and cooling to 0° C., 25 ml. 0.02M osmium tetroxide solution in tert.-butanol and 23.6 ml. (170 mmole) 70% aqueous tert.-butyl hydroperoxide. The reaction mixture is left to stand for 12 days at 4° C., 200 ml. dichloromethane and 140 ml. 10% aqueous sodium sulphite solution are added thereto, stirred until no more hydroperoxide is detectable, the organic phase is separated off, the aqueous phase is extracted twice with 100 ml. amounts of dichloromethane and the combined organic phases are washed with aqueous sodium chloride solution. The organic phase contains a mixture of threo-ethyl 5-(2-chlorophenyl)-4,5-dihydroxy-3-methoxy-2(E)-pentenoate and threo-5-(2-chlorophenylhydroxymethyl)-4-methoxy-2(5H)-furanone. By evaporation, the ring closure is completed to give, after recrystallisation from tert.-butyl methyl ether, 19.4 g. (76.2 mmole) of pure product (m.p. 149°–151° C.) which is thin layer chromatographically and IR-spectroscopically identical with the product obtained according to Example 63a. Yield: 72.6%.

Process variant c

As in the case of variant b but, instead of the ethyl ester, there is used benzyl 5-(2-chlorophenyl)-3-methoxy-2(E),4(E)-pentadienoate. Yield to threo-5-(2-chlorophenylhydroxymethyl)-4-methoxy-2(5H)-furanone after recrystallisation from ethanol: 67.5%. M.p. 149°–151° C.

Process variant d

To a solution of 26.7 g. (100 mmole) ethyl 5-(2-chlorophenyl)-3-methoxy-2(E),4(E)-pentadienoate in 360 ml. acetone are added, with stirring, 10 ml. 0.02 molar osmium tetroxide solution in tert.-butanol and a solution of 14.9 g (110 mmole) N-methylmorpholine N-oxide hydrate in 30 ml. water and stirred for 4 days at ambient temperature. By stirring with 5.2 g. (50 mmole) sodium bisulphite dissolved in 50 ml. water, excess N-oxide is reduced and the pH is adjusted with 1M sulphuric acid to 4. Acetone is stripped off in a vacuum and the remaining aqueous mixture is extracted twice with 200 ml. amounts of dichloromethane. The extract is washed free from N-methylmorpholine with dilute sulphuric acid and water and, after drying over anhydrous sodium sulphate, is concentrated in a vacuum. 18.13 g. threo-5-(2-chlorophenylhydroxymethyl)-4-methoxy-2(5H)-furanone crystallise out. Evaporation of the filtrate and recrystallisation from ethyl acetate gives a further 1.20 g. of pure product. Yield: 19.33 g. (75.9 mmole)≙75.9%

Process variant e

As in the case of variant d but the reaction is carried out, instead of in acetone, in the two-phase system butanone/water and instead of 110 mmole there are used 160 mmole N-methylmorpholine N-oxide. Yield: 76.2%.

Process variant f

As in the case of variant d but in the two-phase system dichloromethane/water. Yield: 66.7%.

Process variant g

A mixture of 23.6 g. (80 mmole) sec.-butyl 5-(2-chlorophenyl)-3-methoxy-2(E),4(E)-pentadienoate, 200 ml. butanone, 15 ml. 0.02M osmium tetroxide solution in tert.-butanol, 17.6 g. (160 mmole) N-methylmorpholine N-oxide hydrate and 50 ml. water is stirred for 7 days at ambient temperature. After the addition of 100 ml. dichloromethane, the reaction mixture is stirred with 100 ml. 2% aqueous sodium bisulphite solution, the organic phase is separated off and washed twice with 100 ml. amounts of 0.5M hydrochloric acid and five times with 100 ml. amounts of water. The organic phase contains a mixture of threo-sec.-butyl 5-(2-chlorophenyl)-4,5-dihydroxy-3-methoxy-2(E)-pentenoate and threo-5-(2-chlorophenylhydroxymethyl)-4-methoxy-2(5H)-furanone. By the addition of 0.1 ml. 32% hydrochloric acid and evaporation of the organic phase, the ring closure is completed to give, after recrystallisation from diethyl ether, 10.66 g. (41.9 mmole) threo-5-(2-chlorophenylhydroxymethyl)-4-methoxy-2(5H)-furanone. Yield: 52.3%.

In the same way, instead of the sec.-butyl ester, there can be used the corresponding methyl, isopropyl or tert.-butyl esters.

Analogously to the process variants a to g described in Example 64, by the oxidation of the 3-alkoxy-5-phenyl-2(E),4(E)-pentadienoic acid derivatives described in Examples 6 to 63, there are prepared the threo-4-alkoxy-5-phenylhydroxymethyl-2(5H)-furanone derivatives given in Table 6. Table 7 contains the results of the elementary analyses and Table 8 the $^1$H-NMR spectroscopic data.

TABLE 6

| Example No. | threo-4-alkoxy-5-phenylhydroxymethyl-2(5H)—furanones designation | Variant | yield [%] | m.p. [°C.] (recrystallised from) |
|---|---|---|---|---|
| 65 | threo-4-methoxy-5-phenylhydroxymethyl-2(5H)—furanone | a | 46 | 157 |
|  |  | b | 49 | (dichloromethane) |
|  |  | d | 59 |  |
| 66 | threo-5-(2-chlorophenyl- | a | 24 | 114–116 |

TABLE 6-continued threo-4-alkoxy-5-phenylhydroxymethyl-2(5H)—furanones

| Example No. | designation | Variant | yield [%] | m.p. [°C.] (recrystallised from) |
|---|---|---|---|---|
| | hydroxymethyl)-4-ethoxy-2(5H)—furanone | | | (isopropanol) |
| 67 | threo-5-(4-chlorophenyl-hydroxymethyl)-4-methoxy-2(5H)—furanone | b | 47 | 148–150 (dichloromethane) |
| 68 | threo-5-(2-bromophenyl-hydroxymethyl)-4-methoxy-2(5H)—furanone | d | 85 | 162–164 (dichloromethane) |
| 69 | threo-5-(3-bromophenyl-hydroxymethyl)-4-methoxy-2(5H)—furanone | b | 50 | 167–168 (acetone/ethanol) |
| 70 | threo-5-(2-fluorophenyl-hydroxymethyl)-4-methoxy-2(5H)—furanone | d | 87 | 130–133 (dichloromethane) |
| 71 | threo-4-methoxy-5-(2-trifluoromethylphenyl-hydroxymethyl)-2-(5H)—furanone | b | 62 | 166–167 (ethanol/water) |
| 72 | threo-4-methoxy-5-(3-trifluoromethylphenyl-hydroxymethyl)-2(5H)—furanone | b | 27 | 128–129 (ethanol/water) |
| 73 | threo-4-methoxy-5-(4-trifluoromethylphenyl-hydroxymethyl)-2(5H)—furanone | b | 28 | 171 (methanol) |
| 74 | threo-4-methoxy-5-(2-nitrophenylhydroxymethyl)-2(5H)—furanone | a | 10 | 170–172 (ethyl acetate) |
| 75 | threo-4-methoxy-5-(3-nitrophenylhydroxymethyl)-2(5H)—furanone | a | 21 | 149–151 (ethyl acetate) |
| 76 | threo-5-(2,5-dimethylphenylhydroxymethyl)-4-methoxy-2(5H)—furanone | b | 47 | 171–173 (ethanol) |
| 77 | threo-5-[(2-chloro-5-methylphenyl)-hydroxymethyl]4-methoxy-2(5H)—furanone | b | 71 | 174–175 (methanol) |
| 78 | threo-5-(2,3-dichlorophenylhydroxymethyl)-4-methoxy-2(5H)—furanone | e | 75 | 161–162 (methanol) |
| 79 | threo-5-(2,4-dichlorophenylhydroxymethyl)-4-methoxy-2(5H)—furanone | a b e | 38 87 55 | 174 (dichloromethane) |
| 80 | threo-5-(2,4-dichlorophenylhydroxymethyl)-4-ethoxy-2(5H)—furanone | b | 72 | 133 (isopropanol) |
| 81 | threo-5-(2,5-dichlorophenylhydroxymethyl)-4-methoxy-2(5H)—furanone | a b | 15 70 | 187 (dichloromethane) |
| 82 | threo-5-(2,5-dichlorophenylhydroxymethyl)-4-ethoxy-2(5H)—furanone | b | 70 | 175–178 (isopropanol) |
| 83 | threo-5-(3,4-dichlorophenylhydroxymethyl)-4-methoxy-2(5H)—furanone | b | 53 | 158–159 (ethyl acetate) |
| 84 | threo-5-(3,5-dichlorophenylhydroxymethyl)-4-methoxy-2(5H)—furanone | b | 62 | 177–179 (ethanol) |
| 85 | threo-5-[bis-(trifluoromethyl)-phenyl-hydroxymethyl]-4-methoxy-2(5H)—furanone | e | 52 | 191–194 (ethyl acetate) |
| 86 | threo-5-[2-chloro-5-trifluoromethylphenyl)-hydroxymethyl]-4-methoxy-2(5H)—furanone | e | 69 | 196–199 (ethyl acetate) |
| 87 | threo-5-[(4-chloro-2-trifluoromethylphenyl)-hydroxymethyl]-4-methoxy-2(5H)—furanone | e | 76 | 166–172 (ethyl acetate) |
| 88 | threo-5-[(4-bromo-2-chlorophenyl)-hydroxymethyl]-4-methoxy-2(5H)—furanone | e | 84 | 173–176 (methanol) |

TABLE 7

Elementary analyses

| Example No. | sum formula molecular weight | % calc. C % found C | H H | other |
|---|---|---|---|---|
| 65 | $C_{12}H_{12}O_4$ 220.23 | 65.45 65.59 | 5.49 5.59 | |
| 66 | $C_{13}H_{13}ClO_4$ 268.69 | 58.11 58.03 | 4.88 4.93 | Cl (13.19) 13.5 |
| 67 | $C_{12}H_{11}ClO_4$ 254.67 | 56.59 56.26 | 4.35 4.14 | Cl (13.92) 14.1 |
| 68 | $C_{12}H_{11}BrO_4$ 299.13 | 48.18 48.18 | 3.71 3.65 | Br (26.71) 27.2 |
| 69 | $C_{12}H_{11}BrO_4$ 299.13 | 48.18 48.24 | 3.71 3.81 | Br (26.71) 27.5 |
| 70 | $C_{12}H_{11}FO_4$ 238.22 | 60.50 60.22 | 4.66 4.29 | F (7.98) 7.6 |
| 71 | $C_{13}H_{11}F_3O_4$ 288.23 | 54.17 54.37 | 3.85 4.02 | F (19.78) |
| 72 | $C_{13}H_{11}F_3O_4$ 288.23 | 54.17 54.25 | 3.85 4.09 | F (19.78) 20.0 |
| 73 | $C_{13}H_{11}F_3O_4$ 288.23 | 54.17 54.92 | 3.85 4.02 | F (19.78) 19.0 |
| 74 | $C_{12}H_{11}NO_6$ 265.23 | 54.34 54.48 | 4.18 4.29 | N (5.28) 5.15 |
| 75 | $C_{12}H_{11}NO_6$ 265.23 | 54.34 54.26 | 4.18 4.28 | N (5.28) 5.45 |
| 76 | $C_{14}H_{16}O_4$ 248.29 | 67.73 67.78 | 6.50 6.88 | |
| 77 | $C_{13}H_{13}ClO_4$ 268.69 | 58.11 58.00 | 4.88 4.90 | Cl (13.19) 13.8 |
| 78 | $C_{12}H_{10}Cl_2O_4$ 289.12 | 49.85 49.86 | 3.49 3.46 | Cl (24.53) 24.8 |
| 79 | $C_{12}H_{10}Cl_2O_4$ 289.12 | 49.85 49.89 | 3.49 3.46 | Cl (24.53) 24.6 |
| 80 | $C_{13}H_{12}Cl_2O_4$ 303.15 | 51.51 51.23 | 3.99 3.94 | Cl (23.39) 23.0 |
| 81 | $C_{12}H_{10}Cl_2O_4$ 289.12 | 49.85 49.62 | 3.49 3.35 | Cl (24.53) 24.6 |
| 82 | $C_{13}H_{12}Cl_2O_4$ 303.15 | 51.51 51.09 | 3.99 3.84 | Cl (23.39) 23.0 |
| 83 | $C_{12}H_{10}Cl_2O_4$ 289.12 | 49.85 49.62 | 3.49 3.36 | Cl (24.53) 24.3 |
| 84 | $C_{12}H_{10}Cl_2O_4$ 289.12 | 49.85 49.82 | 3.49 3.70 | Cl (24.53) 24.6 |
| 85 | $C_{14}H_{10}F_6O_4$ 356.23 | 47.21 47.16 | 2.83 2.90 | F (32.00) |
| 86 | $C_{13}H_{10}ClF_3O_4$ 322.67 | 48.39 47.88 | 3.12 3.00 | Cl (10.99) 10.8 |
| 87 | $C_{13}H_{10}ClF_3O_4$ 322.67 | 48.39 48.34 | 3.12 3.05 | Cl (10.99) 11.3 |
| 88 | $C_{12}H_{10}BrClO_4$ 333.57 | 43.21 43.12 | 3.02 2.95 | Br (23.96) 23.5 Cl (10.63) 10.2 |

TABLE 8

300 MHz - $^1H$—NMR, δ[ppm]

| Example No. | 4-OCH₃(s) | H-3 J₃/₅ [Hz] | H-5 J₅/α[Hz] | H-α J_{α/OH}[Hz] | α-OH |
|---|---|---|---|---|---|
| 65 | 3.88 | 5.369(s) | 5.091(d) | 4.903(t) | 5.740(d) |

TABLE 8-continued

| | | 300 MHz - $^1$H—NMR, δ[ppm] | | | |
|---|---|---|---|---|---|
| Example No. | 4-OCH$_3$(s) | H-3 J$_{3/5}$ [Hz] | H-5 J$_{5/\alpha}$[Hz] | H-α J$_{\alpha/OH}$[Hz] | α-OH |
| | | — | 1.7 | 5.75 | |
| 66 | 4.149(m) (4-O—CH$_2$—) | 5.364(d) 1.17 | 4.960(dd) 2.35 | 5.218(dd) 5.28 | 5.866(d) |
| 67 | 3.88 | 5.378(s) — | 5.095(d) ca. 1.5 | 4.92(t) 5.3 | 5.864(d) |
| 68 | 3.992 | 5.437(s) — | 5.000(d) 1.47 | 5.181(t) 5.28 | 5.972(d) |
| 69 | 3.898 | 5.393(d) 0.89 | 5.137(d) 1.33 | 4.928(dd) 5.75 | 5.877(d) |
| 70 | 3.904 | 5.412(d) 0.89 | 4.993(d) 1.3 | 5.159(dd) 5.75 | 5.877(d) |
| 71 | 3.898 | 5.452(s) — | 4.861(s) — | 5.167(bs) 5.31 | 6.099(d) |
| 72 | 3.89 | 5.344(d) 0.89 | 5.150(dd) 2.21 | 5.028(dd) 5.31 | 5.869(d) |
| 73 | 3.90 | 5.353(d) 0.89 | 5.130(dd) 2.21 | 5.015(dd) 5.75 | 5.849(d) |
| 75 | 3.917 | 5.419(d) 0.88 | 5.230(dd) 2.21 | 5.108(dd) 5.75 | 6.107(d) |
| 76 | 3.90 | 5.380(d) 0.89 | 4.987(bs) 1.77 | 5.031(dd) 4.87 | 5.551(d) |
| 77 | 3.910 | 5.387(d) 0.88 | 4.966(dd) 1.77 | 5.191(dd) 5.75 | 5.798(d) |
| 78 | 3.92 | 5.407(d) 1.17 | 5.022(dd) 2.34 | 5.259(dd) 5.29 | 5.993(d) |
| 79 | 3.92 | 5.446(s) — | 5.005(bs) 1.77 | 5.186(dd) 5.75 | 6.064(d) |
| 80 | 4.15(m) (4-0—CH$_2$—) | 5.336(d) 0.89 | 4.954(dd) 2.65 | 5.179(dd) 5.75 | 5.958(d) |
| 81 | 3.925 | 5.458(s) — | 5.035(bs) 1.77 | 5.175(dd) 5.75 | 6.131(d) |
| 82 | 4.160(m) (4-O—CH$_2$—) | 5.380(d) 0.89 | 4.989(dd) 2.65 | 5.174(dd) 5.75 | 6.035(d) |
| 83 | 3.901 | 5.400(s) — | 5.153(d) 1.77 | 4.96(dd) 5.75 | 5.976(d) |
| 84 | 3.897 | 5.363(d) 0.89 | 5.152(t) 2.21 | 4.952(t) 5.75 | 5.941(d) |
| 86 | 3.93 | 5.428(d) 1.33 | 5.060(t) 1.77 | 5.276(dd) 5.75 | 6.134(d) |
| 88 | 3.91 | 5.399(d) 1.17 | 4.977(d) 2.34 | 5.179(dd) 5.87 | 5.951(d) | abbreviations:
s = singlet,
bs = broad singlet,
d = doublet,
dd = doubled doublet,
t = triplet,
m = multiplet

EXAMPLE 89 threo-5-(2-Chlorophenylhydroxymethyl)-4-methoxy-5-methyl-2(5H)-furanone

Process A

A mixture of 28 g. ethyl 5-(2-chlorophenyl)-3-methoxy-4-methyl-2(E),4(E)-pentadienoate (crude product from Example 61), 250 ml. tetrahydrofuran and 50 ml. water is mixed with 25 ml. 0.02M osmium tetroxide solution in tert.-butanol and 10.7 g. sodium chlorate and heated under reflux for 4 days, with stirring. A further 25 ml. 0.02M osmium tetroxide solution and 10.7 g. sodium chlorate are added thereto and the reaction mixture is boiled under reflux for a further 3 days. In spite of incomplete oxidation, it is worked up. After cooling and adding 100 ml. dichloromethane, the inorganic components are washed out with water, the dichloromethane phase is dried over anhydrous sodium sulphate, evaporated and the residue recrystallised from ethyl acetate to give 1.463 g. of pure threo-5-(2-chlorophenylhydroxymethyl)-4-methoxy-5-methyl-2(5H)-furanone; m.p. 181°-184° C. TLC on silica gel F 254 with chloroform/methanol (95/5 v/v) gives an Rf of 0.37.

Analysis: C$_{13}$H$_{13}$ClO$_4$ (268.69) calc.: C (58.11), H (4.88), Cl (13.19) found: C (57.52), H (4.67), Cl (12.9)

Process B

With stirring, cooling to −77° C. and under a nitrogen atmosphere, to a solution of 8.30 g. (82 mmole) diisopropylamine in 150 ml. tetrahydrofuran are added dropwise 50 ml. of a 1.64 molar solution of n-butyl lithium in hexane and 10.52 g. (82 mmole) 1,3-dimethyl-3,4,5,6-tetrahydro-2(1H)-pyrimidinone (DMPU). Subsequently, a solution of 10.5 g. (82 mmole) 4-methoxy-5-methyl-2(5H)-furanone in 80 ml. tetrahydrofuran is added dropwise thereto, stirred for 30 minutes and a solution of 11.84 g. (82 mmole) 2-chlorobenzaldehyde in 50 ml. tetrahydrofuran added thereto. With stirring, it is allowed to come to 0° C. within 16 hours, hydrolysed by the dropwise addition of 50 ml. water and adjusted with 2M hydrochloric acid to pH 5.5. The organic phase is separated off and evaporated and the aqueous phase is extracted three times with 100 ml. amounts of diethyl ether. Evaporate and ether phases are combined, washed with water to remove DMPU, dried over anhydrous sodium sulphate and evaporated. The residue is separated by column chromatography on 400 g. silica gel with chloroform/methanol (98/2 v/v) as eluent. The fractions with Rf (chloroform/methanol; 95/5 v/v) of 0.37 give, after evaporation and recrystallisation from tert.-butyl methyl ether/dichloromethane, 5.3 g. (19.7 mmole) of pure threo-5-(2-chlorophenylhydroxymethyl)-4-methoxy-5-methyl-2(5H)-furanone (m.p. 192°-194° C.) which, thin layer chromatographically and IR-spectroscopically, is identical with the product obtained according to process A.

Analysis: $C_{13}H_{13}ClO_4$ (268.69) calc.: C (58.11), H (4.88), Cl (13.19) found: C (58.05), H (4.81), Cl (13.2)

The fractions with an Rf of 0.48 give, after evaporation and recrystallisation from toluene, 2.64 g. (9.84 mole) pure erythro-5-(2-chlorophenylhydroxymethyl)-4-methoxy-5-methyl-2(5)-furanone; m.p. 153°-155° C.

Analysis: $C_{13}H_{13}ClO_4$ (268.69) calc.: C (58.11), H (4.88), Cl (13.19) found: C (58.02), H (4.87), Cl (13.3)

EXAMPLE 90 threo-5-(2-Chlorophenylhydroxymethyl)-4-methoxy-2(5H)-furanone

With cooling to −70° C., stirring and under nitrogen atmosphere, to a solution of 49.9 ml. (327 mmole) diisopropylamine in 500 ml. anhydrous tetrahydrofuran are added dropwise 200 ml. of a 1.64 molar solution of n-butyl lithium in hexane, 84 g. (655 mmole) 1,3-dimethyl-3,4,5,6-tetrahydro-2(1H)-pyrimidinone and a solution of 37.4 g. (327 mmole) 4-methoxy-2(5H)-furanone in 300 ml. tetrahydrofuran. After stirring for 30 minutes at −55° C., there is added dropwise thereto a solution of 46 g. (327 mmole) 2-chlorobenzaldehyde and 5.8 ml. water in 100 ml. tetrahydrofuran, followed by stirring for 16 hours with gradual warming to 0° C. After hydrolysis with 200 ml. water, adjustment to pH 5.5 with 2M hydrochloric acid and phase separation, the organic phase is evaporated, the aqueous phase is extracted twice with 300 ml. amounts of diethyl ether, evaporate and ether phases are combined, washed three times with 300 ml. water and evaporated. The oily crude product, consisting of a mixture of threo- and erythro-isomers, becomes crystalline after trituration with carbon tetrachloride. Repeated fractional recrystallisation from ethyl acetate gives 41.5 g. (163 mmole) pure threo-5-(2-chlorophenylhydroxymethyl)-4-methoxy-2(5H)-furanone; m.p. 140°-145° C.; Rf=0.35 (TLC, silica gel F 254; chloroform/methanol 95/5 v/v). The product is thin layer chromatographically, NMR- and IR-spectroscopically identical with that prepared in Example 64.

From the mother liquors of the crystallisation, there are obtained 5.0 g. (20 mmole) pure erythro-5-(2-chlorophenylhydroxymethyl)-4-methoxy-2(5H)-furanone; m.p. 159°-161° C. (recrystallised from ethyl acetate); Rf=0.45.

Analysis: $C_{12}H_{11}ClO_4$ (254.67) calc.: C (56.59), H (4.35), Cl (13.92) found: C (56.80), H (4.50), Cl (13.9) 300 MHz-$^1$H-NMR: 7.27-7.67 (4H, m, aromat. protons), 6.205 (1H, d $J_{OH/H\alpha}$=5.0 Hz, α-OH), 5.310 (1H, s, H-3), 5.292 (1H, dd, $J_{H\alpha/H-5}$=2.7 Hz, Hα), 5.113 (1H, d, H-5), 3.73 (3H, s, OCH$_3$).

Further concentration of the mother liquors gives another 18.7 g. (73 mmole) of a crystalline mixture of the threo- and erythro-isomers which was not further separated.

EXAMPLE 91

4-Ethoxy-2(5H)-furanone

A mixture of 34.2 g. (300 mmole) 4-methoxy-2(5H)-furanone, 200 ml. ethanol and 30 mmole sodium ethoxide is stirred in an autoclave under a nitrogen atmosphere for 24 hours at 120° C. After cooling, it is filtered over 100 g. silica gel, the filtrate is evaporated and the residue is distilled twice at 10 mbar over a Vigreux column to give 21.6 g. (169 mmole) 4-ethoxy-2(5H)-furanone; b.p.$_{10}$=135°-137° C. Yield: 56%.

EXAMPLE 92

4-Propoxy-2(5H)-furanone

Preparation analogous to Example 91 from 4-methoxy-2(5H)-furanone and propanol; b.p.$_{10}$ 143°-145° C. Yield: 39%.

Analysis: $C_7H_{10}O_3$ (142.16) calc.: C (59.14), H (7.09) found: C (59.18), H (7.36)

EXAMPLES 93-105

Analogously to the processes given in Examples 89B and 90, there were prepared further threo-4-alkoxy-5-[α-hydroxy-ω-(subst.)-phenylalkyl]-2(5H)-furanones which were separated from the erythro-isomers accompanying them. Designation, melting points and Rf values determined thin layer chromatographically on silica gel F 254 are summarised in the following Table 9, analytical data in Table 10 and $^1$H-NMR-spectroscopic data in Table 11. The data of the erythro-isomers are also given insofar as they are available.

TABLE 9 threo-4-alkoxy-5-[αhydroxy-ω-(subst.)-phenylalkyl]-2(5H)—furanones

| Example No. | designation | Rf (eluent) | m.p. [°C.] (recryst. from) |
|---|---|---|---|
| 93 | threo-4-methoxy-5-(2-methylphenylhydroxymethyl)-2(5H)—furanone | 0.45 (acetone/toluene 1/1) | 174-176 (isopropanol) |
| 94 | threo-4-methoxy-5-(3-methylphenylhydroxymethyl)-2(5H)—furanone | 0.39 (toluene/isopropanol 5/1) | 127-130 (dichloromethane/pentane) |
| | [erythro isomer: | 0.45 | 139-141 ] (toluene) |
| 95 | threo-4-methoxy-5-(4-methylphenylhydroxymethyl)-2(5H)—furanone | 0.45 (toluene/acetone 1/1) | 148-151.5 (isopropanol/pentane) |
| | [erythro isomer: | 0.47 | 143-147 ] isopropanol) |
| 96 | threo-5-(3-fluorophenylhydroxymethyl)-4-methoxy-2-(5H)—furanone | 0.30 (CHCl$_3$/CH$_3$OH 95/5) | 123-126 (dichloromethane/pentane) |
| 97 | threo-5-(4-fluorophenylhydroxymethyl)-4-methoxy-2(5H)—furanone | 0.26 (CHCl$_3$/CH$_3$OH 98/2) | 141 (toluene/tert. butyl methyl ether) |
| | [erythro isomer: | 0.26 | 141-143] (toluene/tert.-butyl methyl ether) |
| 98 | threo-5-(3-chlorophenylhydroxymethyl)-4-methoxy-2(5H)—furanone | 0.41 (toluene/acetone 1/1) | 150-152 (chloroform/pentane) |

TABLE 9-continued threo-4-alkoxy-5-[αhydroxy-ω-(subst.)-phenylalkyl]-2(5H)—furanones

| Example No. | designation | Rf (eluent) | m.p. [°C.] (recryst. from) |
|---|---|---|---|
|  | [erythro isomer | 0.45 | 121–126] (chloroform/pentane) |
| 99 | threo-5-(2-chlorophenyl-hydroxymethyl)-4-propoxy-2-(5H)—furanone | 0.39 (CHCl$_3$/CH$_3$OH 98/2) | 103–105 (CCl$_4$) |
|  | [erythro isomer: | 0.39 | 147–149] (ethyl acetate) |
| 100 | threo-5-(4-bromophenyl-hydroxymethyl)-4-methoxy-2(5H)—furanone | 0.46 (toluene/acetone 1/1) | 157–158 (CCl$_4$/ethyl acetate) |
|  | [erythro isomer: | 0.49 | 149–150] (ethyl acetate) |
| 101 | threo-4-methoxy-5-(4-nitrophenylphenylhydroxy-methoxy-2(5H)—furanone | 0.42 (toluene/acetone 1/1) | 226–228 (iso-propanol) |
|  | [erythro isomer: | 0.45 | 180–184] (ethyl acetate) |
| 102 | threo-5-(2-chloro-6-fluorophenylhydroxy-methyl)-4-methoxy-2(5H)—furanone | 0.58 (CHCl$_3$/CH$_3$OH 95/5) | 129–133 (CCl$_4$/pentane) |
|  | [erythro isomer: | 0.54 | 151–155] (CCl$_4$/iso-propanol) |
| 103 | threo-5-(2,6-dichloro-phenylhydroxymethiyl)-4-methoxy-2(5H)—furanone | 0.54 (CHCl$_3$/CH$_3$OH 95/5) | 176–180 (toluene/acetone) |
|  | [erythro isomer: | 0.63 | 153–158] (ethyl acetate) |
| 104 | threo-4-methoxy-5-(α-hydroxy-β-phenylethyl)-2(5H)—furanone (contaminated by erythro isomer) | 0.8 (CHCl$_3$/CH$_3$OH 7/3) | 79–84 (benzene) |
| 105 | threo-4-methoxy-5-(α-hydroxy-γ-phenylpropyl)-2(5H)—furanone | 0.45 (acetone/toluene 1/1) | 179–181 (CH$_3$OH/acetone) |

TABLE 10

Elementary analyses

| Example No. | sum formula molecular weight | % calc. C % found C | H H | other other |
|---|---|---|---|---|
| 93 | C$_{13}$H$_{14}$O$_4$ 234.25 | 66.66 66.91 | 6.02 6.42 |  |
| 94 | C$_{13}$H$_{14}$O$_4$ 234.25 (erythro: | 66.66 66.62 66.87 | 6.02 6.43 6.03) |  |
| 95 | C$_{13}$H$_{14}$O$_4$ 234.25 (erythro: | 66.66 66.54 66.92 | 6.02 6.38 6.10) |  |
| 96 | C$_{12}$H$_{11}$FO$_4$ 238.22 | 60.50 60.55 | 4.66 4.90 | F (7.98) 7.50 |
| 98 | C$_{12}$H$_{11}$FO$_4$ 238.22 (erythro: | 60.50 60.31 60.39 | 4.66 4.59 4.75 | F (7.98) 7.6 7.6) |
| 98 | C$_{12}$H$_{11}$ClO$_4$ 254.67 (erythro: | 56.59 56.11 56.50 | 4.35 4.33 4.32 | Cl (13.92) 14.6 14.3) |
| 99 | C$_{14}$H$_{15}$ClO$_4$ 282.73 (erythro: | 59.48 59.36 59.80 | 5.35 5.44 5.52 | Cl (12.54) 12.5) |
| 100 | C$_{12}$H$_{11}$BrO$_4$ 299.13 (erythro: | 48.18 47.92 47.28 | 3.71 3.80 3.67 | Br (26.71) 26.8 26.6) |
| 101 | C$_{12}$H$_{11}$NO$_6$ 265.23 (erythro: | 54.34 54.77 54.27 | 4.18 4.15 4.24 | N (5.28) 5.13 5.08) |
| 102 | C$_{12}$H$_{10}$ClFO$_4$ 272.66 (erythro: | 52.86 52.71 52.02 | 3.70 3.60 3.63 | Cl (13.00) 13.1 13.5) |
| 103 | C$_{12}$H$_{10}$Cl$_2$O$_4$ 289.12 (erythro: | 49.85 49.78 49.77 | 3.49 3.45 3.57 | Cl (24.53) 24.4 24.4) |
| 104 | C$_{13}$H$_{14}$O 234.25 | 66.66 66.06 | 6.02 6.16 |  |
| 105 | C$_{14}$H$_{16}$O$_4$ 248.29 | 67.73 68.11 | 6.50 6.70 |  |

TABLE 11

300 MHz-$^1$H—NMR, δ[ppm]

| Example No. | 4-OCH$_3$(s) | H-3 J$_{3/5}$ [Hz] | H-5 J$_{5/α}$ [Hz] | Hα J$_{α/OH}$ [Hz] | α-OH |
|---|---|---|---|---|---|
| 93 | 3.904 | 5.390(d) 0.88 | 5.015(bs) 1.77 | 5.07(dd) 5.31 | 5.599(d) |
| 94 | 3.89 | 5.36 (d) 0.8 | 5.07 (d) 2 | 4.86(dd) 6 | 5.68 (d) |
| [erythro: | 3.75 | 5.15 (s) — | 5.14 (d) 3.0 | 4.89(dd) 4.9 | 5.88(d)] |
| 95 | 3.89 | 5.35 (d) 0.8 | 5.04 (d) 2.2 | 4.86(dd) 5.6 | 5.65 (d) |
| [erythro: | 3.75 | 5.144(s) — | 5.138(d) 3 | 4.89(dd) 4.9 | 5.87(d)] |
| 96 | 3.90 | 5.39 (d) 0.9 | 5.14(dd) 2 | 4.94(dd) 5.6 | 5.87(d) |
| 97 | 3.90 | 5.36 (d) 0.89 | 5.07(dd) 2.21 | 4.91(dd) 5.31 | 5.78(d) |
| [erythro: | 3.77 | 5.18 (d) 0.89 | 5.16 (d) 3.10 | 4.96(dd) 4.87 | 6.02(d)] |
| 98 | 3.87 | 5.39 (d) 0.88 | 5.14(dd) 2.2 | 4.94(dd) 5.75 | 5.86(d) |
| [erythro: | 3.76 | 5.23 (d) 0.88 | 5.20 (d) 2.7 | 4.98(dd) 5.3 | 6.14(d)] |
| 99 | 4.06(m) (4-O—CH$_2$—) | 5.42 (d) 1 | 4.99(dd) 2.5 | 5.22(dd) 5.8 | 5.97(d) |
| [erythro: | 3.88(t) | 5.29 (s) — | 5.10 (d) 2 | 5.30(dd) 5 |  |

TABLE 11-continued

| Example No. | 4-OCH$_3$(s) | H-3 J$_{3/5}$ [Hz] | H-5 J$_{5/\alpha}$ [Hz] | H$\alpha$ J$_{\alpha/OH}$ [Hz] | $\alpha$-OH |
|---|---|---|---|---|---|
| | | 300 MHz-$^1$H—NMR, δ[ppm] | | | |
| 100 | 3.89 | 5.37 (d) 0.88 | 5.09 (d) 1.7 | 4.90(dd) 5.31 | 5.83(d) |
| [erythro: | 3.76 | 5.19(s) — | 5.17 (d) 2.21 | 4.94(dd) 5.15 | 6.05(d)] |
| 101 | 3.91 | 5.41 (d) 0.89 | 5.20(dd) 1.77 | 5.08 (dd) 5.75 | 6.07(d) |
| [erythro: | 3.77 | 5.25 (s) — | 5.26 (d) 2.65 | 5.14 (dd) 5.31 | 6.32(d)] |
| 102 | 3.73 | 5.45 (s) — | 5.12 (d) 6.19 | 5.16 (t) 4.87 | 6.19(d) |
| [erythro: | 3.86 | 5.38 (s) | 5.15 (d) 6.19 | 5.24 (t) 5.75 | 6.21(d)] |
| 103 | 3.99 | 5.41 (s) | 5.32 (d) 7.96 | 5.37(dd) 4.87 | 6.22(d) |
| [erythro: | 3.64 | 5.44 (s) | 5.35 (d) 7.08 | 5.27(dd) 5.31 | 6.27(d)] |
| 105 | 3.85 | 5.33 (d) 0.9 | 4.85 (t) ca. 1.8 | 3.67 (m) | 5 (m) |

Abbreviations as in Table 8.

EXAMPLE 106 threo-4-Ethoxy-5-[methoxy-(2,4-dichlorophenyl)-methyl]-2(5H)-furanone

A mixture of 3.0 g. (9.9 mmole) threo-5-(2,4-dichlorophenylhydroxymethyl)-4-ethoxy-2(5H)-furanone, 50 ml. butanone, 9.23 g. (39.8 mmole) silver(I) oxide and 5 ml. (80 mmole) methyl iodide is heated to the boil under reflux for 24 hours, with stirring. The mixture is filtered, the filtrate is evaporated and the oily crude product is recrystallised twice from diethyl ether/petroleum ether to give 2.03 g. (6.4 mmole) threo-4-ethoxy-5-[methoxy-(2,4-dichlorophenyl)-methyl]-2(5H)-furanone; m.p. 110°–114° C. Yield: 64.6%.

Analysis: C$_{14}$H$_{14}$Cl$_2$O$_4$ (317.18) calc.: C (53.02), H (4.45), Cl (22.35) found: C (53.16), H (4.60), Cl (22.4) 300 MHz-$^1$H-NMR: 7.45–7.7 (3H, m, aromat. protons), 5.40 (1H, d, J$_{H-3/H-5}$=0.88 Hz, H-3), 5.05 (1H, dd, J$_{H-5/H\alpha}$=3.10 Hz, H-5), 4.86 (1H, d, H$\alpha$), 4.17 (2H, ABX$_3$-system, 4—OCH$_2$—). 3.20 (3H, s, $\alpha$-OCH$_3$), 1.30 (3H, J$_{CH3/OCH2}$=7.07 Hz, CH$_3$).

EXAMPLE 107 threo-4-Methoxy-5-[methoxymethoxy-(2-chlorophenyl)-methyl]-2(5H)-furanone

A mixture of 12.7 g. (50 mmole) threo-5-(2-chlorophenylhydroxymethyl)-4-methoxy-2(5H)-furanone, 100 ml. dimethoxymethane, 1.7 g. (20 mmole) lithium bromide and 0.95 g. (5 mmole) p-toluenesulphonic acid hydrate is heated to the boil under reflux for 4 days, while stirring. It is then evaporated, mixed with 50 ml. dichloromethane, washed with water free of lithium bromide and p-toluenesulphonic acid, the organic phase is evaporated and the crude product is recrystallised twice from methanol to give 10.68 g. (35.75 mmole) of the methoxymethyl ether; m.p. 141°–143° C. Yield: 71.7%.

Analysis: C$_{14}$H$_{15}$ClO$_5$ (298.73) calc.: C (56.29), H (5.06), Cl (11.87) found: C (56.52), H (5.10), Cl (11.9) 300 MHz-$^1$NMR: 7.3–7.6 (4H, m, aromat. protons), 5.47 (1H, d, J$_{H-3/H-5}$=0.88 Hz, H-3), 5.32 (1H, d, H$_{H\alpha/H-5}$=2.65 Hz, H index alpha H=$\alpha$), 5.09 Hz (1H, dd, H-5), 4.55 and 4.42 (2H, AB-system, J$_{AB}$=7.08 Hz, O—CH$_2$—O), 3.94 (3H, s, 4—OCH$_3$), 3.20 (3H, s, $\omega$—OCH$_3$).

EXAMPLE 108 threo-4-Methoxy-5-[methoxyethoxymethoxy-(2-chlorophenyl)-methyl]-2(5H)-furanone

A solution of 10.2 g. (40 mmole) threo-5-(2-chlorophenylhydroxymethyl)-4-methoxy-2(5H)-furanone in 250 ml. dichloromethane is successively mixed with 27 ml. (238 mmole) methoxyethoxymethyl chloride and 40 ml. (234 mmole) N-ethyldiisopropylamine and heated to the boil under reflux for 30 hours. After cooling, it is washed with, in all, 260 ml. 1M hydrochloric acid and twice with 50 ml. amounts of water, dried over anhydrous sodium sulphate, evaporated and the oily crude product recrystallised twice from ethanol to give 9.86 g. (28.8 mmole) of the methoxyethoxymethyl ether; m.p. 102°–104° C. Yield: 72%.

Analysis: C$_{16}$H$_{19}$ClO$_6$ (342.78) calc.: C (56.07), H (5.59), Cl (10.34) found: C (55.72); H (5.60), Cl (10.2)

EXAMPLES 109 TO 124

According to the methods of etherification and transacetalisation described in Examples 106 to 108, there are prepared the ether and acetal derivatives of the previously described threo-4-alkoxy-5-[(subst.)phenylhydroxymethyl]-2(5H)-furanones set out in the following Table 12. The analytical data are summarised in Table 13.

TABLE 12

Ether and acetal derivatives

| Example No. | designation | m.p. [°C.] (recryst. from) |
|---|---|---|
| 109 | threo-4-methoxy-5-[methoxy-(phenyl)-methyl]-2(5H)-furanone | 91–95 (ether/heptane) |
| 110 | threo-4-methoxy-5-[methoxy-(2-chlorophenyl)-methyl]-2(5H)-furanone | 118–120 (ether/pentane) |
| 111 | threo-4-methoxy-5-[methoxy-(2,4-dichlorophenyl)-methyl]-2(5H)-furanone | 124–125 (ether/petroleum ether |
| 112 | threo-4-methoxy-5-[methoxy-(2,5-dichlorophenyl)-methyl]-2(5H)-furanone | 95 (ether/petroleum ether) |
| 113 | threo-4-methoxy-5-[methoxymethoxy-(phenyl)-methyl]-2(5H)-furanone | 93–96 (methanol) |
| 114 | threo-4-methoxy-5-[methoxymethoxy-(2,4-dichlorophenyl)- | 142–145 (methanol) |

TABLE 12-continued

Ether and acetal derivatives

| Example No. | designation | m.p. [°C.] (recryst. from) |
|---|---|---|
|  | methyl]-2(5H)-furanone |  |
| 115 | threo-4-methoxy-5-[methoxy-methoxy-(2-fluorophenyl)-methyl]-2(5H)-furanone | 102–104 (methanol) |
| 116 | threo-4-methoxy-5-[methoxy-methoxy-(2-methylphenyl)-methyl]-2(5H)-furanone | 141–144 (ethyl acetate) |
| 117 | threo-4-methoxy-5-[methoxy-methoxy-(4-bromophenyl)-methyl]-2(5H)-furanone | 144–146 (ethanol) |
| 118 | threo-4-methoxy-5-[methoxy-methoxy-(2-bromophenyl)-methyl]-2(5H)-furanone | 160–161 (ethanol) |
| 119 | threo-4-methoxy-5-[methoxy-methoxy-(4-chlorophenyl)-methyl]-2(5H)-furanone | 130 (methanol) |
| 120 | threo-4-methoxy-5-[methoxy-ethoxymethoxy-(2,4-dichloro-phenyl)-methyl]-2(5H)-furanone | 104–107 (ethanol) |
| 121 | threo-5-[1',2'-dimethoxyethoxy-(2-chlorophenyl)-methyl]-4-methoxy-2(5H)-furanone | 131–134 (ethanol) |
| 122 | threo-5-[1'-ethoxypropoxy-(2-chlorophenyl)-methyl]-4-methoxy-2-(5H)-furanone | 106–108 (ether/pentane) |
| 123 | threo-4-methoxy-5-[methoxy-(2-fluorophenyl)-methyl]-2(5H)-furanone | 106–108 (ether) |
| 124 | threo-4-methoxy-5-[methoxy-(2-bromophenyl)-methyl]-2(5H)-furanone | 123–125 (ether/methanol) |

TABLE 13

Elementary analyses

| Example No. | sum formula molecular weight | % calc. C % found C | H H | other other |
|---|---|---|---|---|
| 109 | $C_{13}H_{14}O_4$ 234.25 | 66.66 66.84 | 6.02 6.25 |  |
| 110 | $C_{13}H_{13}ClO_5$ 268.69 | 58.11 58.02 | 4.88 5.01 | Cl (13.19) 13.5 |
| 111 | $C_{13}H_{12}Cl_2O_5$ 303.15 | 51.50 51.56 | 3.99 3.97 | Cl (23.39) 23.5 |
| 112 | $C_{13}H_{12}Cl_2O_5$ 303.15 | 51.50 52.02 | 3.99 4.16 | Cl (23.39) 23.4 |
| 113 | $C_{14}H_{16}O_5$ 264.29 | 63.63 63.65 | 6.10 6.09 |  |
| 114 | $C_{14}H_{14}Cl_2O_5$ 333.18 | 50.47 50.36 | 4.23 4.22 | Cl (21.28) 20.9 |
| 115 | $C_{14}H_{15}FO_5$ 282.28 | 59.57 59.32 | 5.36 5.49 | F (6.7) 7.3 |
| 116 | $C_{15}H_{18}O_5$ 278.31 | 64.74 64.71 | 6.52 6.71 |  |
| 117 | $C_{14}H_{15}BrO_5$ 343.19 | 49.00 48.44 | 4.41 4.36 | Br (23.28) 22.3 |
| 118 | $C_{14}H_{15}BrO_5$ 343.19 | 49.00 48.38 | 4.41 4.27 | Br (23.28) 23.2 |
| 119 | $C_{14}H_{15}ClO_5$ 298.73 | 56.29 55.47 | 5.06 5.00 | Cl (11.87) 11.8 |
| 120 | $C_{16}H_{18}Cl_2O_6$ 377.23 | 50.95 50.62 | 4.81 4.76 | Cl (18.20) 18.2 |
| 121 | $C_{16}H_{19}ClO_6$ 342.78 | 56.07 55.81 | 5.59 5.47 | Cl (10.34) 10.3 |
| 122 | $C_{17}H_{21}ClO_5$ 340.81 | 59.91 59.62 | 6.21 6.10 | Cl (10.40) 10.6 |
| 123 | $C_{13}H_{13}FO_4$ 252.24 | 61.90 61.75 | 5.19 5.16 | F (7.53) |
| 124 | $C_{13}H_{13}BrO_4$ 313.15 | 49.86 49.84 | 4.18 4.18 | Br (25.52) 25.2 |

For the determination of the anticonvulsive/antiepileptic activity of the compounds according to the present invention, there was used the method described by E. A. Swinyard et al., J. Pharmacol. exp. Therapeut. 106, 319–330/1952 and by L. A. Woodbury et al., Arch. int. Pharmacodyn., 92, 97–107/1952. Two male mice (NMRI) with a body weight of 20–25 g. is applied, via corneal electrodes, an alternating current of 50 Hz and 50 mA for 0.2 sec. (HSE-shock stimulation apparatus; type 207). The maximum electroshock spasm (MES) consists of a tonic extension of the rear extremities, clonic twitch and loss of consciousness. The activity criterion is taken as being the inhibition of the extensor spasm by the compounds according to the present invention. Before the experiments, the mice had free access to feed and water. The test substances were administered orally as suspensions in 0.2% agar by stomach tubes; the control animals received adequate volumes of agar. 1 hour after administration, the test for protective action against MES was carried out.

The following Table 14 sets out the results of the MES test in the case of dosages of 50 to 150 mg. of the compounds according to the present invention per kg. of body weight in comparison with conventional anti-epileptics. As percentage action there is given the percentage proportion of those animals which, in the case of the MES test, were protected 100% against the extensor spasm.

The following Table 15 sets out, as ED 50 values, those dosages of the compounds according to the present invention and of conventional anti-epileptics which, in the MES test, are able to protect 50% of the animals against the extensor spasm 1 hour after administration. The determination of the ED 50 values and of the confidence limits (5% probability of error) was made according to Lichtfield and Wilcoxon (J. Pharmacol. exp. Therapeut., 96, 99/1949), in each case with 4 to 5 animal groups each of 8 to 10 animals per dosage stage.

During the above-described experiments, the animals were observed during the whole of the experimental period (up to 4 hours) for signs of substance-caused changes of behaviour and neurotoxicity (motility, muscle tonus, respiratory frequency, body temperature and general behaviour). Up to a dosage of 100 mg./kg., in the case of all the tested compounds, no neurotoxic symptoms were ascertained. In comparison hereto, the following Table 16 sets out the lower limiting dosages of conventional anticonvulsives which, after oral administration, bring about neurotoxicity symptoms in mice.

In the case of all compounds according to the present invention, in oral dosages of up to 300 mg./kg., no mortality was ascertained of the mice. Orientating toxicological investigations of the compounds according to Examples 64, 65, 79 and 81 on rats showed, up to an oral dosage of 1000 mg./kg., no mortality of the animals.

The present investigations show, in effect, a good anticonvulsive action and outstanding therapeutic breadth of the compounds according to the present invention.

TABLE 14

Results of the MES test:

| Substance according to Example No. | dose [mg/kg] | number of animals in the experiment | protective action [%] after 1 hr. |
|---|---|---|---|
| 64 | 100 | 8 | 100 |
| 65 | 100 | 24 | 79 |
| 66 | 100 | 10 | 100 |
| 67 | 100 | 8 | 75 |
| 68 | 100 | 10 | 100 |
| 69 | 100 | 10 | 70 |

TABLE 14-continued

Results of the MES test:

| Substance according to Example No. | dose [mg/kg] | number of animals in the experiment | protective action [%] after 1 hr. |
|---|---|---|---|
| 70 | 100 | 10 | 100 |
| 71 | 100 | 10 | 100 |
| 72 | 100 | 10 | 80 |
| 73 | 100 | 10 | 60 |
| 74 | 100 | 10 | 100 |
| 79 | 100 | 10 | 60 |
| 80 | 100 | 10 | 90 |
| 81 | 100 | 10 | 100 |
| 82 | 150 | 10 | 90 |
| 83 | 100 | 18 | 50 |
| 84 | 100 | 10 | 70 |
| 86 | 50 | 10 | 100 |
| 87 | 100 | 10 | 40 |
| 88 | 100 | 10 | 80 |
| 89 | 100 | 10 | 100 |
| 93 | 100 | 8 | 37.5 |
| 96 | 100 | 8 | 62.5 |
| 98 | 100 | 8 | 25 |
| 99 | 100 | 10 | 90 |
| 100 | 100 | 10 | 100 |
| 102 | 100 | 8 | 62.5 |
| 103 | 100 | 8 | 100 |
| 104 | 100 | 8 | 37.5 |
| 105 | 100 | 8 | 12.5 |
| 106 | 100 | 10 | 30 |
| 107 | 100 | 10 | 100 |
| 108 | 100 | 10 | 70 |
| 109 | 100 | 10 | 40 |
| 110 | 100 | 10 | 100 |
| 111 | 100 | 10 | 100 |
| 112 | 100 | 10 | 100 |
| 113 | 100 | 10 | 100 |
| 114 | 100 | 10 | 10 |
| 115 | 100 | 10 | 100 |
| 116 | 100 | 10 | 70 |
| 118 | 100 | 10 | 100 |
| 121 | 50 | 10 | 70 |
| 122 | 50 | 10 | 100 |
| 123 | 50 | 10 | 100 |
| 124 | 50 | 10 | 100 |
| carbamazepine | 50 | 10 | 100 |
| Diazepam | 50 | 10 | 100 |
| diphenylhydantoin | 50 | 10 | 100 |
| Ethosuximide | 100 | 10 | 0 |
| phenobarbital | 100 | 10 | 100 |
| valproic acid | 100 | 10 | 0 |

TABLE 15

ED 50 values in the MES test

| substance according to Example No. | number of animals | ED 50 [mg/kg] | confidence limit [mg/kg] |
|---|---|---|---|
| 64 | 50 | 19.75 | (17.10–22.81) |
| 65 | 60 | 69.0 | (63.07–75.49) |
| 67 | 60 | 73.5 | (63.86–84.60) |
| 68 | 60 | 23.5 | (23.38–27.10) |
| 69 | 50 | 93 | (84.69–102.10) |
| 70 | 60 | 22.0 | (19.08–25.37) |
| 79 | 60 | 82.5 | (75.61–90.01) |
| 81 | 40 | 19.5 | (13.47–28.24) |
| 96 | 60 | 74.0 | (63.46–86.28) |
| 98 | 60 | 84.5 | (78.24–91.26) |
| 100 | 60 | 67.0 | (60.31–74.44) |
| 103 | 60 | 37.0 | (28.70–47.50) |
| 107 | 60 | 24.5 | (22.15–27.10) |
| 110 | 60 | 27.5 | (25.45–29.71) |
| carbamazepine | 60 | 14.6 | (12.36–17.24) |
| Diazepam | 40 | 13.8 | (9.93–19.18) |
| diphenylhydantoin (4 h) | 40 | 9.1 | (7.23–11.47) |
| Ethosuximide | 50 | >250 | |
| pentobarbital (s.c.) | 60 | 35.2 | (31.9–38.8) |
| phenobarbital | 50 | 19.2 | (16.29–22.61) |
| valproic acid (i.p.) | 50 | 205 | (169–248) |

TABLE 16

Neurotoxic limiting dose in the mouse

| substance | dose p.o. [mg/kg] |
|---|---|
| Carbamazepine | 100 |
| Diazepam | 40 |
| diphenylhydantoin | 100 |
| Ethosuximide | 500 |
| pentobarbital | 60 |
| phenobarbital | 60 |
| valproic acid | 350 |
| compounds according to the invention according to Examples 64–124 | all > 100 |

Examples for the preparation of pharmaceutical compositions of the compounds according to the present invention

A. Tablets

For the production of tablets each of 250 mg. individual weight which, depending upon the desired strength of action, contained 5 to 100 mg. of active substance, there are required:

| | |
|---|---|
| compound according to the present invention | 200 to 4000 g. |
| cellulose powder | 2000 g. |
| maize starch | 1200 g. |
| colloidal silicic acid | 80 g. |
| magnesium stearate | 20 g. |
| milk sugar ad | 10000 g. |

Active material and adjuvant materials are mixed homogeneously and pressed in the usual way to give tablets each of 250 mg. weight and 9 mm. diameter. If desired, the tablets can be provided with a film coating.

B. Capsules

For the production of capsules which, depending upon the desired strength of action, contain 5 to 100 mg. of active material, there are required:

| | |
|---|---|
| compound according to the present invention | 500 to 10000 g. |
| maize starch | 1000 g. |
| colloidal silicic acid | 300 g. |
| magnesium stearate | 50 g. |
| cellulose powder ad | 20000 g. |

The finely powdered materials are homogeneously mixed and filled into hard gelatine capsules of size 2 in the amount of 200 mg. per capsule.

C. Juice

For the production of a juice with a content of 0.035 to 0.7 wt.% of active material, depending upon the desired strength of action, there are required:

| compound according to the present invention | 35 to 700 g. |
|---|---|
| propylene glycol | 20000 g. |
| glycerol | 20000 g. |
| methyl cellulose | 1000 g. |
| sodium cyclamate | 500 g. |
| saccharin sodium | 50 g. |
| demineralised water ad | 100 000 g. |

The active material is finely ground and stirred homogeneously into the solution of the adjuvant materials.

D. Suppository

For the production of suppositories each of 3 g. individual weight, containing 5 to 100 mg. of active material, depending upon the strength of action desired, there are required:

| compound according to the present invention | 50 to 1000 g. |
|---|---|
| colloidal silicic acid | 60 g. |
| lecithin | 150 g. |
| hard fat ad | 30000 g. |

The finely ground active material is homogeneously stirred into a melt of the adjuvant materials and cast into suppositories of 3 g. individual weight.

We claim:

1. 5-Arylalkyl-4-alkoxy-2(5H)-furanones of the formula:

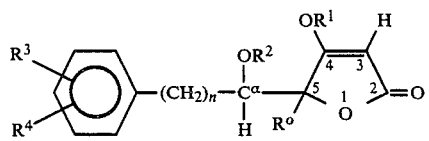

wherein the oxygen atoms on C-5 and C-α, relative to one another, are in the threo-position and wherein n is 0, 1 or 2, $R^o$ is a hydrogen atom or an alkyl radical containing up to 3 carbon atoms, $R^1$ a straight-chained or branched alkyl radical containing up to 5 carbon atoms, $R^2$ is a hydrogen atom, an alkyl radical containing up to 3 carbon atoms or the radical

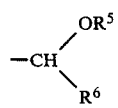

wherein $R^5$ is an alkyl radical containing up to 5 carbon atoms or an ethoxyethyl or methoxyethyl radical and $R^6$ is a hydrogen atom, an alkyl radical containing up to 5 carbon atoms or a methoxymethyl radical, $R^3$ and $R^4$, independently of one another, are hydrogen, fluorine, chlorine or bromine atoms, alkyl radicals containing up to 3 carbon atoms, perfluoroalkyl radicals containing up to 3 carbon atoms, a difluoromethoxy radical or a nitro group, with the exclusion of those compounds of formula (I) wherein $R^2$ is H or $CH_3$ when n=0 or 2, $R^o$=H, $R^1$=$CH_3$, $R^3$=H and $R^4$=H.

2. 4-Methoxy-5-phenylhydroxymethyl-2(5H)-furanones of the formula:

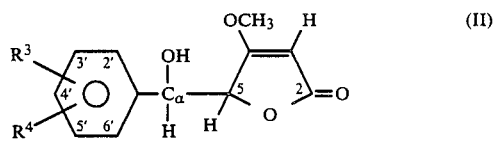

wherein the oxygen atoms on C-5 and C-α, relative to one another, are in the threo-position and wherein one of the two symbols $R^3$ and $R^4$ signifies a hydrogen atom and the other a fluorine, chlorine or bromine atom present in the 2'-position or a methyl, trifluoromethyl or nitro group present in the 2'-position.

3. 4-Methoxy-5-phenylhydroxymethyl-2(5H)-furanones of the formula (II), wherein the oxygen atoms on C-5 and C-α, relative to one another, are in the threo-position and wherein one of the two symbols $R^3$ and $R^4$ signifies a fluorine, chlorine or bromine atom or a trifluoromethyl radical, in each case in the 2'-position, and the other signifies a chlorine or bromine atom or a trifluoromethyl radical, in each case in the 4'-, 5'- or 6'-position.

4. 4-Methoxy-5-[methoxy-(phenyl)-methyl]-2(5H)-furanones of the formula:

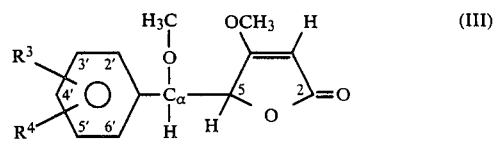

wherein the oxygen atoms on C-5 and C-α, relative to one another, are in the threo-position and wherein $R^3$ and $R^4$ have the same meanings as in claim 1, with the exclusion of those compounds of the formula (III) wherein both symbols $R^3$ and $R^4$ represent hydrogen atoms.

5. 4-Methoxy-5-phenylmethyl-2(5H)-furanones of the formula:

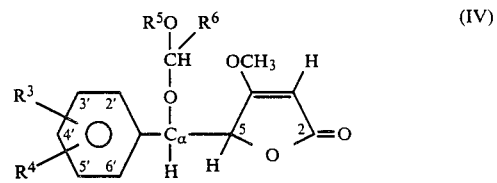

wherein the oxygen atoms on C-5 and C-α, relative to one another, are in the threo-position and wherein $R^5$ is a methyl or methoxyethyl radical and $R^3$, $R^4$ and $R^6$ have the meanings given in claim 1.

6. threo-5-(2'-Chlorophenylhydroxymethyl)-4-methoxy-2(5H)-furanone.

7. threo-5-(2'-Bromophenylhydroxymethyl)-4-methoxy-2(5H)-furanone.

8. threo-5-(2'-Fluorophenylhydroxymethyl)-4-methoxy-2(5H)-furanone.

9. threo-5-(2'-Trifluoromethylphenylhydroxymethyl)-4-methoxy-2(5H)-furanone.

10. threo-5-(2',5'-Dichlorophenyl)hydroxymethyl-4-methoxy-2(5H)-furanone.

11. threo-5-(2',4'-Dichlorophenyl)hydroxymethyl-4-methoxy-2(5H)-furanone.

12. threo-4-Methoxy-5-[methoxymethoxy-(2'-chlorophenyl)-methyl]-2(5H)-furanone.

13. threo-4-Methoxy-5-[methoxymethoxy-(2'-bromophenyl)-methyl]-2(5H)-furanone.

14. threo-4-Methoxy-5-[methoxymethoxy-(2'-fluorophenyl)-methyl]-2(5H)-furanone.

15. threo-4-Methoxy-5-[methoxymethoxy-(2'-trifluoromethylphenyl)-methyl]-2(5H)-furanone.

16. threo-4-Methoxy-5-[methoxy-(2'-chlorophenyl)-methyl]-2(5H)-furanone.

17. A pharmaceutical composition containing at least one compound of the formula I as claimed in claim 1, with the exclusion of those compounds of said formula I wherein $R^2$ is H or $CH_3$ when n=0 or 2, $R^0$=H, $R^1$=$CH_3$, $R^3$=H and $R^4$=H, and a pharmacologically inert excipient.

* * * * *